US006995015B1

(12) United States Patent
Subramanian et al.

(10) Patent No.: US 6,995,015 B1
(45) Date of Patent: *Feb. 7, 2006

(54) PATHOGEN-RESISTANT GRAPE PLANTS

(75) Inventors: Jayasankar Subramanian, Tavares, FL (US); Zhijian Li, Altamonde Springs, FL (US); Dennis J. Gray, Howey-in-the-Hills, FL (US)

(73) Assignee: University of Florida, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/570,217

(22) Filed: May 12, 2000

Related U.S. Application Data

(60) Provisional application No. 60/134,275, filed on May 14, 1999, provisional application No. 60/148,251, filed on Aug. 11, 1999.

(51) Int. Cl.
*A01H 1/04* (2006.01)
(52) U.S. Cl. .................... 435/430.1; 435/430; 800/276
(58) Field of Classification Search ................ 435/418, 435/430.1, 430; 800/295, 276, 301
See application file for complete search history.

(56) References Cited

U.S. PATENT DOCUMENTS

| | | | |
|---|---|---|---|
| 4,532,733 A | 8/1985 | Krul ........................ | 435/430.1 |
| 4,937,970 A | 7/1990 | Guan et al. .................. | 800/276 |
| 5,084,082 A | 1/1992 | Sebastian ..................... | 504/212 |
| 5,238,835 A | 8/1993 | McKersie et al. .......... | 800/298 |
| 5,524,802 A | 6/1996 | Benson et al. .............. | 224/194 |
| 5,583,036 A | 12/1996 | Rangan et al. .............. | 435/427 |
| 5,648,594 A | 7/1997 | Davis et al. ................ | 800/323 |
| 5,696,999 A | 12/1997 | Matsushima et al. ......... | 396/55 |
| 5,834,292 A | 11/1998 | Rangan et al. .............. | 800/268 |
| 5,856,177 A | 1/1999 | Grula et al. ............. | 435/320.1 |
| 5,859,321 A | 1/1999 | Rangan et al. .............. | 800/301 |
| 5,874,662 A | 2/1999 | Rangan et al. .............. | 800/276 |
| 5,914,270 A | 6/1999 | Coutos-Thevenot et al. .......................... | 435/430 |
| 5,968,827 A | 10/1999 | Mauro et al. ................ | 435/410 |
| 6,455,312 B1 | 9/2002 | Gray et al. .............. | 435/430.1 |
| 2003/0005489 A1 * | 1/2003 | Gray et al. .................. | 800/298 |

FOREIGN PATENT DOCUMENTS

| | | |
|---|---|---|
| FR | 2 710 234 | 9/1993 |
| WO | WO 93/11660 | 6/1993 |
| WO | WO 93/23529 | 11/1993 |
| WO | WO 94/13787 | 6/1994 |
| WO | WO 95/19102 | 7/1995 |
| WO | WO 97/49277 | 12/1997 |
| WO | WO 99/11133 | 3/1999 |
| WO | WO 99/59398 | 11/1999 |
| WO | WO 00/70054 | 11/2000 |

OTHER PUBLICATIONS

Brooks et al, Register of New Fruit and Nut Varieties, 1972, American Society for Horticultural Science, vol. 45, pp. 226, 232, 233, 243.*
Tattersall et al, Identification and Characterization of a Fruit-Specific, Thaumatin-Like Protein That Accumulates at Very high Levels in Conjunction with the Onset of Sugar Accumulation and Berry Softening in Grapes, 1997, Plant Physiology, vol. 114, pgs.*
Margaret E. Daub, A Cell Culture Approach for the Development of Disease Resistance: Studies on the Phytotoxin Cercosporin, Jun. 1984, HortScience, vol. 19, No. 3, pp. 18-23.*
Concise Encyclopedia Biochemistry, Second Ed. 1988, Scott and Eagleson eds., Walter de Gruyter publisher, pp 461.*
Subramanian J., "Selection and Characterization of Resistance in Mango (*Mangifera indica* L.) Embryogenic Cultures to the Phytotoxin produced by *Colletotrichum Gloeosporioides* Penz," University of Florida, 1995.
Published U.S. Appl. No.: US 2003-0005489 A1.
Busam et al., "Characterization and Expression of Caffeoyl-Coenzyme A 3-O-Methyltransferase Proposed for the Induced Resistance Response of *Vitis vinifera* L," *Plant Physiol.* 115:1039-1046 (1997).
Compton et al., "Effects of Sucrose and Methylglyoxal Bis-(guanyldrazone) on Controlling Grape Somatic Embryogenesis," *Vitis* 35:1-6 (1996).
Coutos-Thevenot et al., "Four 9-kDa Proteins Excreted by Somatic Embryos of Grapevine are Isoforms of Lipid-Transfer Proteins," *Eur. J. Biochem.* 217:885-889 (1993).
Coutos-Thevenot et al., "Somatic Embryogenesis from Grapevine Cells. I-Improvement of Embryo Development by Changes in Culture Conditions," *Plant Cell, Tissue and Organ Cult.* 29:125-133 (1992).
Goebel-Tourand et al., "Arrest of Somatic Embryo Development in Grapevine: Histological Characterization and the Effect of ABA, BAP and Zeatin in Stimulating Plantlet Development," *Plant Cell, Tissue and Organ Cult.* 33:91-103 (1993).
Goussard et al., "The Elimination of Fanleaf Virus from Grapevines Using in vitro Somatic Embryogenesis Combined with Heat Therapy," *S. Afr. J. Ecol. Vitic.* 13:81-83 (1992).

(Continued)

*Primary Examiner*—David H Kruse
(74) *Attorney, Agent, or Firm*—Timothy H. Van Dyke; Beusse Brownlee Wolter Mora & Maire

(57) ABSTRACT

The invention features a method of producing a grape somatic embryo having resistance to a plant pathogen, the method including the steps of (a) culturing a grape somatic embryo in a first liquid culture medium that includes a plant growth regulator and a phytotoxin from a plant pathogen; (b) exchanging the first liquid culture medium for a second liquid culture medium not including the phytotoxin; (c) recovering a living grape cell or grape cell cluster from the second liquid culture, the living cell or cell cluster being resistant to the pathogen; and (d) culturing the grape cell or grape cell cluster in a third culture medium to produce a grape somatic embryo.

5 Claims, 10 Drawing Sheets

OTHER PUBLICATIONS

Goussard et al., "The Effectiveness of in vitro Somatic Embryogenesis in Eliminating Fanleaf Virus and Leafroll Associated Viruses from Grapevines," *S. Afr. J. Ecol. Vitic.* 12:77-81 (1991).

Gray et al., "In vitro Micropropagation and Plant Establishment of Muscadine Grape Cultivars (*Vitis rotundifolia*)," *Plant Cell, Tissue and Organ Culture* 27:7-14 (1991).

Gray et al., "Initiation and Maintenance of Long Term Somatic Embryogenesis from Anthers and Ovaries of *Vitis longii* 'Microsperma'," *Plant Cell, Tissue and Organ Culture* 9:73-80 (1987).

Gray et al., "Biotechnology of Perennial Fruit Crops," *Grape* 229-262 (1992).

Gray et al., "Somatic Embryogensis and Plant Regeneration from Immature Zygotic Embryos of Muscadine Grape (*Vitis rotundifolia*) Cultivars," *Amer. J. Bot.* 79:542-546 (1992).

Hébert et al., "Optimization of Biolistic Transformation of Embryogenic Grape Cell Suspensions," *Plant Cell Reports* 12:585-589 (1993).

Hébert-Soulé et al., "Phosphinothricin Stimulates Somatic Embryogenesis in Grape (*Vitis* sp. L.)," *Plant Cell Reports* 14:380-384 (1995).

Jayasankar et al., "In vitro Selection of Grape for Resistance to the Anthracnose Fungus, *Elsinoe Ampelina*," *In Vitro Cellular & Devel. Biol. Animal* 34:51A (1998).

Jayasankar et al., "In vitro Selection and Molecular Characterization of Anthracnose Resistance in Grapevine," *In Vitro Cellular & Develop. Biol. Animal* 35:45 (1999).

Jayasankar et al., "In vitro Selection of *Vitis vinifera* 'Chardonnay' with *Elsinoe ampelina* Culture Filtrate is Accompanied by Fungal Resistance and Enhanced Secretion of Chitinase," *Planta* 211:200-208 (2000).

Kikkert et al., "Transgenic Plantlets of 'Chancellor' Grapevine (*Vitis* sp.) from Biolistic Transformation of Embryogenic Cell Suspensions," *Plant Cell Reports* 15:311-316 (1996).

Krastanova et al., "Transformation of Grapevine Rootstocks with the Coat Protein Gene of Grapevine Fanleaf Nepovirus," *Plant Cell Reports* 14:550-554 (1995).

Krul et al., "Formation of Adventitious Embryos in Callus Cultures of Seyval, a French Hybrid Grape," *J. Amer. Soc. Hort. Sci.* 102:360-363 (1977).

Liswidowati et al., "Induction of Stilbene Synthase by *Botrytis Cinerea* in Cultured Grapevine Cells," *Planta* 183:307-314 (1991).

Martinelli et al., "Somatic Embryogenesis from Leaf-and Petiole-Derived Callus of *Vitis rupestris*," *Plant Cell Reports* 12:207-210 (1993).

Matsuta, "Effect of Auxin on Somatic Embryogenesis from Leaf Callus in Grape (*Vitis spp.*)," *Japan J. Breed* 42:879-883 (1992).

Matsuta et al., "Embryogenic Cell Lines from Somatic Embryos of Grape (*Vitis vinifera* L.)," *Plant Cell Reports* 7:684-687 (1989).

Mauro et al., "Stimulation of Somatic Embryogenesis and Plant Regeneration from Anther Culture of *Vitis vinifera* cv. Cabernet-Sauvignon," *Plant Cell Reports* 5:377-380 (1986).

Mauro et al., "High Efficiency Regeneration of Grapevine Plants Transformed with the GFLV Coat Protein Gene," *Plant Science* 112:97-106 (1995).

Mullins et al., "Plantlets from Cultured Anthers of *Vitis* Species and Hybrids," In Proc. of 3$^{rd}$ Int'l Symp. on Grape Breeding, *University of California (Davis)* 111-119 (1980).

Mullins et al., "Somatic Embryos and Plantlets from an Ancient Clone of the Grapevine (cv. Cabernet-Sauvignon) by Apomixis in vitro," *J. Exp. Bot.* 27:1022-1030 (1976).

Newton et al., "The Ontogeny of Somatic Embryos from in vitro Cultured Grapevine Anthers," *S. Afr. J. Ecol. Vitic.* 11:70-75 (1990).

Pearce et al., "Effects of Chilling and ABA on [$^3$H] Gibberellin A$_4$ Metabolism in Somatic Embryos of Grape (*Vitis vinifera* L. x *V. rupestris* Scheele)" *Plant Physiol.* 80:381-385 (1987).

Perl et al., "Establishment of an *Agrobacterium* -Mediated Transformation System for Grape (*Vitis vinifera* L.): The Role of Antioxidants During Grape-*Agrobacterium* Interactions," *Nature Biotechnol.* 14:624-628 (1996).

Perl et al., Regeneration and Transformation of Grape (*Vitis vinifera* L.), *Plant Tissue Cult. and Biotechnol.* 2:187-193 (1996).

Rajasekaran et al., "Embryos and Plantlets from Cultured Anthers of Hybrid Grapevines," *J. Exp. Bot. 30:* 399-407 (1979).

Rajasekaran et al., "Influence of Genotype and Sex-Expression on Formation of Plantlets by Cultured Anthers of Grapevines," *Agronomie* 3:233-238 (1983).

Rajasekaran et al., "Dormancy in Somatic Embryos and Seeds of *Vitis:* Changes in Endogenous Abscisic Acid During Embryogeny and Germination," *Planta* 154:139-144 (1982).

Regner et al., "Somatiche Embryogenese bei Weinreben (*Vitis vinifera*),"*Mitteilungen Klosterneuburg* 46:105-113 (1996).

Reustle et al., "Plant Regeneration of Grapevine (*Vitis sp.*) Protoplasts Isolated from Embryogenic Tissue," *Plant Cell Reports* 15:238-241 (1995).

Robacker, C., "Somatic Embryogenesis and Plant Regeneration from Muscadine Grape Leaf Explants," *HortScience* 28:53-55 (1993).

Salzman et al., "Coordinate Accumulation of Antifungal Proteins and Hexoses Constitutes a Developmentally Controlled Defense Response during Fruit Ripening in Grape," *Plant Pysiol* 117: 465-742, (1998).

Scorza et al., "Producing Transgenic 'Thompson Seedless' Grape (*Vitis vinifera* L.) Plants," *J. Amer. Soc. Hort. Sci.* 121-616-619 (1996).

Srinivasan et al., "High-Frequency Somatic Embryo Production from Unfertilized Ovules of Grapes," *Scientia Horticulturae* 13:245-252 (1980).

Stamp et al., "Somatic Embryogenesis from Leaves and Anthers of Grapevine," *Scientia Horticulturae* 35:235-250 (1988).

Stamp et al., "Proliferative Somatic Embryogenesis from Zygotic Embryos of Grapevine," *J. Amer. Soc. Hort. Sci.* 113:941-945 (1988).

Takeno et al., "Endogenous Gibberellin-Like Substances in Somatic Embryos of Grape (*Vitis vinifera* x *Vitis rupestris*) in Relation to Embryogenesis and the Chilling Requirement for Subsequent Development of Mature Embryos," *Plant Physiol.* 73:803-808 (1983).

* cited by examiner

1 - Marker
2 - ICF from non-selected plant
3 - 6 ICF from selected plant
7 - 8 ECP from embryos of selected lines (internal std)

```
+2              A  N  E  F  T  N    L  L  Y    C  I  Q  K    R  K  K    K  Y  V    I  F  G
     EcoRI
  1  AGAATTCCAA CAGGCCAATG AGTTCACCAA TTTACTGTAC TGCATCCAAA AGAGGAAAAA GAAGTATGTA ATATTTGGTG
     TCTTAAGGTT GTCCGGTTAC TCAAGTGGTT AAATGACATG ACGTAGGTTT TCTCCTTTTT CTTCATACAT TATAAACCAC

+2 V  C  D  V    Y  G  I    H  Q  G  G    I  I  L    G  P  S    G  L  G  K    S  P  A  F  S  K
 81  TGTGTGATGT TTATGGTATT CATCAGGGAG GTATTATCCT GGGACCGTCG GGTTTAGGAA AATCTCCAGC ATTCTCCAAA
     ACACACTACA AATACCATAA GTAGTCCCTC CATAATAGGA CCCTGGCAGC CCAAATCCTT TTAGAGGTCG TAAGAGGTTT

+2 W  V  F  P    E  S  S    I  Y  F    S  Q  T  V    A  L  F    G  C  M    I  F  M  F    L  V  G
161  TGGGTTTTCC CAGAGAGCAG CATTTATTTC AGCCAAACCG TCGCCTTATT TGGGTGCATG ATCTTTATGT TCCTAGTTGG
     ACCCAAAAGG GTCTCTCGTC GTAAATAAAG TCGGTTTGGC AGCGGAATAA ACCCACGTAC TAGAAATACA AGGATCAACC

+2  V  K  M    D  T  H  L    M  R  K    S  G  R    R  G  V  V    I  G  F    C  N  F    F  L  P
241  AGTGAAAATG GATACACATC TGATGAGGAA GTCAGGAAGG AGAGGAGTAG TCATAGGCTT CTGCAACTTC TTCTTGCCAT
     TCACTTTTAC CTATGTGTAG ACTACTCCTT CAGTCCTTCC TCTCCTCATC AGTATCCGAA GACGTTGAAG AAGAACGGTA

+2 L  I  I  V    V  G  L    A  H  N  L    R  K  T    K  T  L    G  H  N  I    S  N  S    I  Y  C
                                                               StyI
321  TGATAATTGT GGTTGGCTTG GCTCACAATC TCAGAAAAAC TAAGACCTTG GGCCACAATA TAAGCAATTC TATTTACTGT
     ACTATTAACA CCAACCGAAC CGAGTGTTAG AGTCTTTTTG ATTCTGGAAC CCGGTGTTAT ATTCGTTAAG ATAAATGACA

+2  V  A  T  L    M  S  M    S  S  S    H  V  I  T    C  L  L    T  D  I    K  I  L  N    S  E  L
401  GTAGCAACAC TGATGAGCAT GAGTTCCTCC CATGTCATTA CTTGCCTTCT AACTGATATC AAGATCCTCA ACTCCGAGCT
     CATCGTTGTG ACTACTCGTA CTCAAGGAGG GTACAGTAAT GAACGGAAGA TTGACTATAG TTCTAGGAGT TGAGGCTCGA

+2    G  R  L    A  L  S  S    S  M  I    S  G  L    C  S  W  T    L  A  L    G  S  Y    V  I  F
481  GGGAAGGTTA GCCCTATCCT CATCTATGAT AAGTGGCCTG TGCAGTTGGA CCCTGGCATT GGGCTCATAT GTAATATTTC
     CCCTTCCAAT CGGGATAGGA GTAGATACTA TTCACCGGAC ACGTCAACCT GGGACGTAA CCCGAGTATA CATTATAAAG

+2 Q  G  S  T    G  Q  Y    E  S  M  L    A  L  S    L  F    I  I  L  V    L  I  I    V  Y  I
                                SphI
561  AAGGCTCAAC TGGTCAGTAT GAAAGCATGC TAGCATTATC CTTGTCATTT ATCATCTTGG TGCTTATCAT TGTATACATT
     TTCCGAGTTG ACCAGTCATA CTTTCGTACG ATCGTAATAG GAACAGTAAA TAGTAGAACC ACGAATAGTA ACATATGTAA

+2 L  R  P  I    M  D  W    M  V  E    Q  T  A  E    G  K  P    I  K  E    S  Y  V  F    S  I  F
641  CTGCGGCCTA TTATGGATTG GATGGTTGAA CAGACTGCTG AAGGAAAACC AATCAAGGAG AGCTATGTCT TTAGCATCTT
     GACGCCGGAT AATACCTAAC CTACCAACTT GTCTGACGAC TTCCTTTTGG TTAGTTCCTC TCGATACAGA AATCGTAGGA

+2  V  M  I    L  G  S  A    F  L  G    E  L  I    G  L
                StyI                                                EcoRI
721  TGTGATGATC TTAGGGAGTG CCTTCCTTGG TGAACTCATT GGCCTGTTGG AATTCTT
     ACACTACTAG AATCCCTCAC GGAAGGAACC ACTTGAGTAA CCGGACAACC TTAAGAA
```

Fig. 9

```
Present study      TVTXGQVASAVGPXISYLQ nsLTP-P4     TVTCGQVASALSPCIDYLQ
         nsLTP     TITCGQVASALSPIINYLQ
   Sorghum LTP-2   XVTCGQVSSAIGPCLSYXX
      Rice LTP-1   XITCGQVNSAVGPCLTYAR Consensus    TVTCGQVASALGPCISYLQ
```

Fig. 11

```
Present study      ATFDILNKXTYTVXA

VVTL1     ATFDILNKCTYTVWA
   Tobacco PR5 E22 ATFDIVNKCTYTVWA
   Tobacco PR5 E2  ATFDIVNQCTYTVWA
         VVOsm     ATFNIQNHGGYTVWA
            GO     ATFNIQNHCPYTVWA Consensus    ATFDILNKCTYTVWA
```

Fig. 12

22 kDa ECP    ATFDILNKXTYTV
22 kDa ICWF   ATFNIQNKGGYTV

Fig. 13

SEQUENCE LISTING

```
<160> NUMBER OF SEQ ID NOS: 6

<210> SEQ ID NO 1
<211> LENGTH: 19
<212> TYPE: PRT
<213> ORGANISM: Vitis vinifera
<220> FEATURE:
```

```
<221> NAME/KEY: VARIANT
<222> LOCATION: (1)...(19)
<223> OTHER INFORMATION: Xaa = Any Amino Acid

<400> SEQUENCE: 1

Thr Val Thr Xaa Gly Gln Val Ala Ser Ala Val Gly Pro Xaa Ile Ser
 1               5                  10                  15

Tyr Leu Gln

<210> SEQ ID NO 2
<211> LENGTH: 15
<212> TYPE: PRT
<213> ORGANISM: Vitis vinifera
<220> FEATURE:
<221> NAME/KEY: VARIANT
<222> LOCATION: (1)...(15)
<223> OTHER INFORMATION: Xaa = Any Amino Acid

<400> SEQUENCE: 2

Ala Thr Phe Asp Ile Leu Asn Lys Xaa Thr Tyr Thr Val Xaa Ala
 1               5                  10                  15

<210> SEQ ID NO 3
<211> LENGTH: 15
<212> TYPE: PRT
<213> ORGANISM: Vitis vinifera
<220> FEATURE:
<221> NAME/KEY: VARIANT
<222> LOCATION: (1)...(15)
<223> OTHER INFORMATION: Xaa = Any Amino Acid

<400> SEQUENCE: 3

Ala Thr Phe Asn Ile Gln Asn Lys Gly Gly Tyr Thr Val Xaa Ala
 1               5                  10                  15

<210> SEQ ID NO 4
<211> LENGTH: 14
<212> TYPE: PRT
<213> ORGANISM: Vitis vinifera

<400> SEQUENCE: 4

Ala Ser Leu Ala Asp Gln Gln Ala Asn Glu Phe Thr Lys Val
 1               5                  10

<210> SEQ ID NO 5
<211> LENGTH: 251
<212> TYPE: PRT
<213> ORGANISM: Vitis vinifera

<400> SEQUENCE: 5

Ala Asn Glu Phe Thr Asn Leu Leu Tyr Cys Ile Gln Lys Arg Lys Lys
 1               5                  10                  15

Lys Tyr Val Ile Phe Gly Val Cys Asp Val Tyr Gly Ile His Gln Gly
                20                  25                  30

Gly Ile Ile Leu Gly Pro Ser Gly Leu Gly Lys Ser Pro Ala Phe Ser
            35                  40                  45

Lys Trp Val Phe Pro Glu Ser Ser Ile Tyr Phe Ser Gln Thr Val Ala
        50                  55                  60

Leu Phe Gly Cys Met Ile Phe Met Phe Leu Val Gly Val Lys Met Asp
65                  70                  75                  80

Thr His Leu Met Arg Lys Ser Gly Arg Arg Gly Val Val Ile Gly Phe
                85                  90                  95
```

```
Cys Asn Phe Phe Leu Pro Leu Ile Ile Val Val Gly Leu Ala His Asn
                100                 105                 110

Leu Arg Lys Thr Lys Thr Leu Gly His Asn Ile Ser Asn Ser Ile Tyr
            115                 120                 125

Cys Val Ala Thr Leu Met Ser Met Ser Ser His Val Ile Thr Cys
    130                 135                 140

Leu Leu Thr Asp Ile Lys Ile Leu Asn Ser Glu Leu Gly Arg Leu Ala
145                 150                 155                 160

Leu Ser Ser Ser Met Ile Ser Gly Leu Cys Ser Trp Thr Leu Ala Leu
                165                 170                 175

Gly Ser Tyr Val Ile Phe Gln Gly Ser Thr Gly Gln Tyr Glu Ser Met
                180                 185                 190

Leu Ala Leu Ser Leu Ser Phe Ile Ile Leu Val Leu Ile Ile Val Tyr
            195                 200                 205

Ile Leu Arg Pro Ile Met Asp Trp Met Val Glu Gln Thr Ala Glu Gly
            210                 215                 220

Lys Pro Ile Lys Glu Ser Tyr Val Phe Ser Ile Phe Val Met Ile Leu
225                 230                 235                 240

Gly Ser Ala Phe Leu Gly Glu Leu Ile Gly Leu
                245                 250
```

<210> SEQ ID NO 6
<211> LENGTH: 777
<212> TYPE: DNA
<213> ORGANISM: Vitis vinifera

<400> SEQUENCE: 6

```
agaattccaa caggccaatg agttcaccaa tttactgtac tgcatccaaa agaggaaaaa      60
gaagtatgta atatttggtg tgtgtgatgt ttatggtatt catcagggag gtattatcct     120
gggaccgtcg ggtttaggaa aatctccagc attctccaaa tgggttttcc cagagagcag     180
catttatttc agccaaaccg tcgccttatt tgggtgcatg atctttatgt tcctagttgg     240
agtgaaaatg gatacacatc tgatgaggaa gtcaggaagg agaggagtag tcataggctt     300
ctgcaacttc ttcttgccat tgataattgt ggttggcttg gctcacaatc tcagaaaaac     360
taagaccttg ggccacaata taagcaattc tatttactgt gtagcaacac tgatgagcat     420
gagttcctcc catgtcatta cttgccttct aactgatatc aagatcctca actccgagct     480
gggaaggtta gccctatcct catctatgat aagtggcctg tgcagttgga ccctggcatt     540
gggctcatat gtaatatttc aaggctcaac tggtcagtat gaaagcatgc tagcattatc     600
cttgtcattt atcatcttgg tgcttatcat tgtatacatt ctgcggccta ttatggattg     660
gatggttgaa cagactgctg aaggaaaacc aatcaaggag agctatgtct ttagcatctt     720
tgtgatgatc ttagggagtg ccttccttgg tgaactcatt ggcctgttgg aattctt       777
```

PATHOGEN-RESISTANT GRAPE PLANTS

CROSS-REFERENCE TO RELATED APPLICATIONS

This application claims benefit to U.S. Provisional Application No. 60/134,275, filed May 14, 1999, and 60/148,251, filed Aug. 11, 1999, each of which is hereby incorporated by reference.

BACKGROUND OF THE INVENTION

This invention relates to plants having an increased level of resistance to a pathogen and to methods for producing them.

Grapevines are a deciduous temperate fruit crop of ancient origin. Grape production ($65 \times 10^6$ metric tons) exceeds that of any other temperate fruit crop, and ranks third after Citrus and banana production. In addition, due to its uses for fresh fruit, juice, jelly, raisins, and wine, grapes surpass all other fruit crops in value. Therefore, successful efforts to improve grapevines are likely to have a major impact on commercial viticulture.

Current methods for improving grapevines are time-consuming and labor intensive. For example, genetic improvement in grapes through conventional breeding is severely limited by a number of factors such as long pre-bearing age and varying ploidy levels. Cultivated grapes are also highly heterozygous and do not generally breed true from seeds. Moreover, grape breeding programs are expensive, long-term projects. Although plant biotechnology is an attractive alternative for genetic improvement in grapes (Kuksova et al., Plant Cell Tiss. Org. Cult. 49:17–27, 1997), in vitro genetic manipulation can be addressed only if there is an effective regeneration system. Accordingly, methods that reduce any of these problems would represent a significant advancement in the art.

SUMMARY OF THE INVENTION

We have discovered methods for growing perennial grape embryogenic cultures and for growing large quantities of somatic grape embryos from such perennial embryogenic cultures in a relatively short period using a liquid suspension culture. Several advantages are provided by the present methods. These approaches, for example, facilitate an extraordinarily high frequency of somatic embryo formation and plant regeneration. Such frequencies have not been previously reported for grapevine regeneration of any known cultivar, and render the method useful for large-scale production of clonal planting stock of grape plants. In addition, the methods produce embryos free of such common abnormalities as fusion and fasciations of somatic embryos. The methods of the invention also result in enhanced embryogenic culture initiation frequency, allowing for the production of highly embryogenic cultures that can then be successfully carried through the subsequent stages of the regeneration process to the whole plant level. Because of these advantages, the methods of the invention are especially useful in the application of biotechnology for the genetic improvement of this crop.

Embryogenic cells that are resistant to a plant pathogen can be selected in vitro using methods of the present invention. From these cells, or from the culture medium, proteins whose expression is upregulated in response to a pathogen (and the nucleic acid molecules encoding them) are identified. The proteins and nucleic acid molecules can then be used to produce pathogen-resistant plants (i.e., a transgenic or non-transgenic plant expressing such a protein) or to increase plant resistance to a pathogen (e.g., by applying recombinant protein to the surface of a plant).

Accordingly, in a first aspect, the invention features a method of producing a grape somatic embryo having resistance to a plant pathogen, the method including the steps of (a) culturing a grape somatic embryo in a first liquid culture medium that includes a plant growth regulator and a phytotoxin from a culture of the plant pathogen; (b) exchanging the first liquid culture medium for a second liquid culture medium not including the phytotoxin; (c) recovering a living grape cell or grape cell cluster from the second liquid culture, the living cell or cell cluster being resistant to the pathogen; and (d) culturing the grape cell or grape cell cluster in a third culture medium to produce a grape somatic embryo.

In a second aspect, the invention features a method for producing a grape plant having resistance to a plant pathogen, the method including the steps of (a) culturing a grape somatic embryo in a first liquid culture medium that includes a plant growth regulator and a phytotoxin from a culture of the plant pathogen; (b) exchanging the first liquid culture medium for a second liquid culture medium not including the phytotoxin; (c) recovering a living grape cell or grape cell cluster from the second liquid culture, the living cell or cell cluster being resistant to the pathogen; (d) culturing the grape cell or grape cell cluster in a third culture medium to produce a grape somatic embryo; and (e) growing a plant from the grape somatic embryo.

In the methods of the first and second aspects, the phytotoxin may be obtained, for example, from a bacterium or fungus. A preferred plant growth regulator in step (a) is an auxin (e.g., 2,4-D, NAA, NOA, or picloram). If desired, the second culture medium may also include a plant growth regulator. In other preferred embodiments, steps (a)–(d) of the method are repeated at least two time, more preferably at least three times, and most preferably at least four or five times. The culture step (a) can be for a day or two, but is preferably for at least four days, six days, or more. In preferred embodiments, the culture step (a) is for at least nine or ten days.

In a third aspect, the invention features a grape plant regenerated from a cell or cell cluster that has been selected in the presence of a phytotoxin from a plant pathogen, wherein the plant has an increased level of resistance to the pathogen relative to a control grape plant regenerated from a cell or cell cluster not selected in the presence of the phytotoxin. The grape plant is preferably expressing a protein at a level that is at least 25% greater than the level of the protein in the control plant, wherein the protein is selected from the group consisting of (i) a protein having a molecular weight of about 8 kDa and including the polypeptide of SEQ ID NO: 1; (ii) a protein having a molecular weight of about 22 kDa and including the polypeptide of SEQ ID NO: 2; (iii) a protein having a molecular weight of about 22 kDa and including the polypeptide of SEQ ID NO: 3; and (iv) a protein having a molecular weight of about 33 kDa and including the polypeptide of SEQ ID NO: 4. More preferably, the grape plant is expressing a protein at a level that is at least 50%, 100%, 200%, 300%, or even 500% greater than the level of the protein in the control plant.

In a fourth aspect, the invention features a transgenic grape plant containing a transgene encoding a polypeptide substantially identical to the polypeptide having the amino acid sequence of SEQ ID NO: 5, wherein the transgene is operably linked to a promoter. In preferred embodiments, the nucleic acid molecule has the nucleotide sequence of SEQ ID NO: 6, and the promoter is a constitutive promoter, an inducible promoter, or a tissue-specific promoter.

In a fifth aspect, the invention features a transgenic grape plant containing a transgene encoding a PR-5 protein that confers on the plant resistance to a pathogen, wherein the nucleic acid molecule is operably linked to a constitutive promoter.

In a sixth aspect, the invention features a transgenic grape plant containing a transgene encoding a thaumatin-like protein that confers on the plant resistance to a pathogen, wherein the nucleic acid molecule is operably linked to a constitutive promoter.

In a seventh aspect, the invention features a transgenic grape plant containing a transgene encoding a lipid transfer protein that confers on the plant resistance to a pathogen, wherein the nucleic acid molecule is operably linked to a constitutive promoter. In a preferred embodiment, the lipid transfer protein is substantially identical to the amino acid of SEQ ID NO: 5.

In an eighth aspect, the invention features a plant component from the plant of the third, fourth, fifth, sixth, or seventh aspect.

In a ninth aspect, the invention features a method of selecting a plant having pathogen resistance. The method includes determining the levels of a protein in the plant, wherein the protein includes an amino acid sequence selected from the group consisting of SEQ ID NO: 1, SEQ ID NO: 2, SEQ ID NO: 3, and SEQ ID NO: 4, and wherein the levels of the protein are directly proportional to the levels of pathogen resistance in the plant. The pathogen may be, for example, a bacterium or fungus.

In a tenth aspect, the invention features a substantially pure polypeptide substantially identical to the sequence of SEQ ID NO: 5. Preferably, the polypeptide, when expressed in a grape plant, confers on the plant increased pathogen resistance relative to the plant not expressing the polypeptide.

In an eleventh aspect, the invention features a substantially pure nucleic acid molecule encoding a polypeptide substantially identical to the sequence of SEQ ID NO: 5. Preferably, the polypeptide, when expressed in a grape plant, confers on the plant increased pathogen resistance relative to the plant not expressing the polypeptide. In one preferred embodiment, the nucleic acid molecule has the sequence of SEQ ID NO: 6.

In a twelfth aspect, the invention features a method of identifying a protein that confers on a plant pathogen resistance. The method includes the steps of (a) culturing a grape somatic embryo in a first liquid culture medium including a plant growth regulator and a phytotoxin from a plant pathogen culture; (b) exchanging the first liquid culture medium for a second liquid culture medium not including the phytotoxin; (c) recovering a grape cell or grape cell cluster from the second liquid culture; (d) culturing the grape cell or grape cell cluster in a third culture medium to produce a grape somatic embryo having resistance to the plant pathogen; (e) recovering the grape somatic embryo having resistance to the plant pathogen; and (f) identifying a protein that is expressed in the grape somatic embryo and that is not expressed in a grape somatic embryo not cultured in a culture medium including the phytotoxin from the plant pathogen culture, wherein the identified protein is a protein that confers on a plant pathogen resistance.

In a thirteenth aspect, the invention features another method for identifying a protein that, when expressed in a grape plant, confers on the plant pathogen resistance, the method including the steps of (a) contacting an embryogenic cell, embryogenic culture, or somatic embryo, with a plant pathogen; and (b) measuring the level of expression of a protein, wherein an increased level of expression of the protein by the embryogenic cell, embryogenic culture, or somatic embryo, relative to an embryogenic cell, embryogenic culture, or somatic embryo not contacted with the plant pathogen, identifies the protein as one that, when expressed in a plant, confers on the plant pathogen resistance. The level of expression may be measured, for example, using SDS-PAGE, ELISA, or Western Blot analysis. Protein level is preferably standardized in comparison to total protein level.

In a fourteenth aspect, the invention features a method for producing a plant having increased resistance to a plant pathogen, the method including overexpressing a protein identified by the method of twelfth aspect or the method of the thirteenth aspect.

In a fifteenth aspect, the invention features a method for decreasing pathogen-mediated damage to a plant, the method including contacting the plant with a recombinant form of a protein that exhibits increased level of expression following contact with a pathogen.

In a sixteenth aspect, the invention features a method for identifying a cell that is expressing a protein that confers pathogen resistance. The method including the steps of (a) contacting a cell with a phytotoxin from a pathogen culture; and (b) monitoring disease resistance of the cell, wherein increased pathogen resistance, relative to a control cell, identifies the cell as a cell that is expressing a protein that confers on the plant resistance to a pathogen.

In a seventeenth aspect, the invention features a substantially pure polypeptide including the amino acid of SEQ ID NO: 1 and having a molecular weight of about 8 kDa as determined by reducing SDS-PAGE, wherein the polypeptide is expressed at an increased level in a grape plant in response to contact with a filtrate of a culture of *Elsinoδ ampelina*.

In an eighteenth aspect, the invention features a substantially pure polypeptide including the amino acid of SEQ ID NO: 3 and having a molecular weight of about 22 kDa as determined by reducing SDS-PAGE, wherein the polypeptide is expressed at an increased level in a grape plant in response to contact with a filtrate of a culture of *Elsinoδ ampelina*.

In a nineteenth aspect, the invention features a DNA molecule that hybridizes to the DNA of SEQ ID NO: 6.

In a twentieth aspect, the invention features a transgenic plant containing a transgene that hybridizes to the DNA of SEQ ID NO: 6 under high stringency conditions.

In a twenty-first aspect, the invention features a regenerated grape plant that is expressing a protein at a level that is at least 25% greater than the level of the protein in a control grape plant regenerated from a cell or cell cluster not selected in the presence of a phytotoxin from a plant pathogen culture, wherein the protein is selected from the group consisting of: (i) a protein having a molecular weight of about 8 kDa and comprising the polypeptide of SEQ ID NO: 1; (ii) a protein having a molecular weight of about 22 kDa and comprising the polypeptide of SEQ ID NO: 2; (iii) a protein having a molecular weight of about 22 kDa and comprising the polypeptide of SEQ ID NO: 3; and (iv) a protein having a molecular weight of about 33 kDa and comprising the polypeptide of SEQ ID NO: 4. Preferably the plant is expressing at least two proteins (and more preferably at least three or even all four) at levels that are at least 25% greater than the level of the protein in a control grape plant.

In a twenty-second aspect, invention features a substantially pure polypeptide comprising the amino acid sequence of SEQ ID NO: 4.

Terms used herein are defined as follows:

By "perennial grape embryogenic culture" is meant an embryogenic culture in which embryogenic cells or cell masses have been repeatedly selected, subcultured, and maintained as an in vitro culture. Such perennial grape embryogenic cultures can be maintained for at least half a year, preferably three years, and most preferably four or more years.

By "embryogenic cell," "embryogenic cell mass," or "embryogenic cultures" is meant a cell or collection of cells having the inherent potential to develop into a somatic embryo and, ultimately, into a plant. Typically such cells have large nuclei and dense cytoplasm. Additionally, such cells are usually totipotent in that they typically possess all of the genetic and structural potential to ultimately become a whole plant.

By "increased level of embryogenesis" is meant a greater capacity to produce an embryogenic cell or embryogenic cell mass in a perennial grape embryogenic culture than the level of a control non-perennial grape embryogenic culture. In general, such an increased level of embryogenesis is at least 20%, preferably at least 50%, more preferably at least 100% and most preferably at least 250% or greater than the level of a control embryogenic culture. The level of embryogenesis is measured using conventional methods.

By "explant" is meant an organ, tissue, or cell derived from a plant and cultured in vitro for the purpose of initiating a plant cell culture or a plant tissue culture. For example, explant grape tissue may be obtained from virtually any part of the plant including, without limitation, anthers, ovaries, ovules, floral tissue, vegetative tissue, tendrils, leaves, roots, nucellar tissue, stems, seeds, protoplasts, pericycle, apical meristem tissue, embryogenic tissue, somatic embryos, and zygotic embryos.

By "plant growth regulator" is meant a compound that affects plant cell growth and division. Preferred plant growth regulators include natural or synthetic auxins or cytokinins. Exemplary auxins include, but are not limited to, NOA, 2,4-D, NAA, IAA, dicamba, and picloram. Exemplary cytokinins include, but are not limited to, BA and zeatin.

By "somatic embryogenesis" is meant the process of initiation and development of embryos in vitro from plant cells and tissues absent sexual reproduction.

By "somatic embryo" is meant an embryo formed in vitro from somatic cells or embryogenic cells by mitotic cell division.

By "mature somatic embryo" is meant a fully-developed embryo with evidence of root and shoot apices and exhibiting a bipolar structure. Preferred mature somatic embryos are those with well-defined cotyledons.

By "plantlet" is meant a small germinating plant derived from a somatic embryo.

By "regeneration" is meant the production of an organ, embryo, or whole plant in plant tissue culture.

By "plant cell" is meant any cell containing a plastid. A plant cell, as used herein, is obtained from, without limitation, seeds, suspension cultures, embryos, meristematic regions, callus tissue, protoplasts, leaves, roots, shoots, somatic and zygotic embryos, as well as any part of a reproductive or vegetative tissue or organ.

By "promoter" is meant a region of nucleic acid, upstream from a translational start codon, which is involved in recognition and binding of RNA polymerase and other proteins to initiate transcription. A "plant promoter" is a promoter capable of initiating transcription in a plant cell, and may or may not be derived from a plant cell.

By "tissue-specific promoter" is meant that the expression from the promoter is directed to a subset of the tissues of the plant. It will be understood that not every cell in a given tissue needs to be expressing from the promoter in order for the promoter to be considered tissue-specific.

By "heterologous" is meant that the nucleic acid molecule originates from a foreign source or, if from the same source, is modified from its original form. Thus, a "heterologous promoter" is a promoter not normally associated with the duplicated enhancer domain of the present invention. Similarly, a heterologous nucleic acid molecule that is modified from its original form or is from a source different from the source from which the promoter to which it is operably linked was derived.

The term "plant" includes any cell having a chloroplast, and can include whole plants, plant organs (e.g., stems, leaves, roots, etc.), seeds, and cells. The class of plants that can be used in the method of the invention is generally as broad as the class of higher plants amenable to transformation techniques, including both monocots and dicots.

By "plant component" is meant a part, segment, or organ obtained from an intact plant or plant cell. Exemplary plant components include, without limitation, somatic embryos, leaves, fruits, scions, cuttings, and rootstocks.

By "phytotoxin" is meant a substance that is capable of killing a plant cell. Phytotoxins are preferably from a pathogen such as a fungus or a bacterium. For use in the present invention, they may be purified or unpurified. In one example, a phytotoxin is present in a filtrate from a culture of a pathogen such as a bacterium or a fungus. The identity of the phytotoxin (e.g., its chemical structure) need not be known for use in the methods of the invention.

By "pathogen" is meant an organism whose infection of viable plant tissue elicits a disease response in the plant tissue. Such pathogens include, without limitation, bacteria and fungi. Plant diseases caused by these pathogens are described in Chapters 11–16 of Agrios, *Plant Pathology*, 3rd ed., Academic Press, Inc., New York, 1988.

Examples of bacterial pathogens include, without limitation, *Agrobacterium vitis, Agrobacterium tumefaciens, Xylella fastidosa*, and *Xanthomonas ampelina*. Examples of fungal pathogens include, without limitation, *Uncinula necator, Plasmopara viticola, Botrytis cinerea, Guignardia bidwellii, Phomophsis viticola, Elsinoë ampelina, Eutypa lata, Armillaria mellea*, and *Verticllium dahliae*.

By "pathogen culture" is meant a culture in which a pathogen has grown. A filtrate of the culture is preferably substantially free of the pathogen.

By "increased level of resistance" is meant a greater level of resistance or tolerance to a disease-causing pathogen or pest in a resistant grapevine (or scion, rootstock, cell, or seed thereof) than the level of resistance or tolerance or both relative to a control plant (i.e., a grapevine that has not been subjected to in vitro selection to any plant pathogen or toxin-containing filtrate thereof). In preferred embodiments, the level of resistance in a resistant plant of the invention is at least 5–10% (and preferably at least 30% or 40%) greater than the resistance of a control plant. In other preferred embodiments, the level of resistance to a disease-causing pathogen is at least 50% greater, 60% greater, and more preferably even more than 75% or even 90% greater than the level of resistance of a control plant; with up to 100% above the level of resistance as compared to the level of resistance of a control plant being most preferred. The level of resistance or tolerance is measured using conventional methods.

For example, the level of resistance to a pathogen may be determined by comparing physical features and characteristics (for example, plant height and weight, or by comparing disease symptoms, for example, delayed lesion development, reduced lesion size, leaf wilting, shriveling, and curling, decay of fruit clusters, water-soaked spots, leaf scorching and marginal burning, and discoloration of cells) of resistant grape plants with control grape plants. Quantitation can be performed on the level of populations. For example, if 4 out of 40 control plants are resistant to a given pathogen, and 20 out of 40 plants of the invention are resistant to that pathogen, than the latter plant is 20/4 or 500% more resistant to the pathogen.

By "transformed" is meant any cell which includes a nucleic acid molecule (for example, a DNA sequence) which is inserted by artifice into a cell and becomes part of the genome of the organism (in either an integrated or extrachromosomal fashion for example, a viral expression construct which includes a subgenomic promoter) which develops from that cell. As used herein, the transformed organisms or cells are generally transformed grapevines or grapevine components and the nucleic acid molecule (for example, a transgene) is inserted by artifice into the nuclear or plastidic compartments of the plant cell.

By "transgene" is meant any piece of a nucleic acid molecule (for example, DNA) which is inserted by artifice into a cell, and becomes part of an organism (or a descendant thereof) by being integrated into the genome or maintained extrachromosomally which develops from that cell. Such a transgene may include a gene which is partly or entirely heterologous (i.e., foreign) to the transgenic organism, or may represent a gene homologous to an endogenous gene of the organism.

By "transgenic plant" is meant a plant containing a transgene. Those in the art will recognize that, once a transgenic plant has been produced, it may be propagated sexually or asexually; if a descendant contains a transgene, it is considered to be a transgenic plant.

By "protein" is meant any combination of two or more covalently-bonded amino acids, regardless of post-translational modifications.

By "PR-5" is meant a protein that is substantially identical to VVTL-1 (SP accession no. O04708) and, when overexpressed in a grape plant, confers on the plant increased pathogen resistance.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "high stringency conditions" is meant hybridization in 2×SSC at 40° C. with a DNA probe length of at least 40 nucleotides. For other definitions of high stringency conditions, see F. Ausubel et al., Current Protocols in Molecular Biology, pp. 6.3.1–6.3.6, John Wiley & Sons, New York, N.Y., 1994, hereby incorporated by reference.

By "substantially pure polypeptide" is meant a polypeptide that has been separated from the components that naturally accompany it. Typically, the polypeptide is substantially pure when it is at least 60%, by weight, free from the proteins and naturally-occurring organic molecules with which it is naturally associated. Preferably, the polypeptide is at least 75%, more preferably at least 90%, and most preferably at least 99%, by weight, pure. A substantially pure polypeptide may be obtained, for example, by extraction from a natural source, by expression of a recombinant nucleic acid encoding the polypeptide, or by chemically synthesizing the protein. Purity can be measured and further enhanced by any appropriate method, e.g., by column chromatography, polyacrylamide gel electrophoresis, or HPLC analysis.

Methods of measuring protein amounts are known in the art. Any of these methods is useful for quantitating the level of total protein or of a specific protein. For example, proteins can be separated by polyacrylamide gel electrophoresis and individual proteins quantitated using densitometry.

A polypeptide is substantially free of naturally associated components when it is separated from those contaminants that accompany it in its natural state. Thus, a polypeptide which is chemically synthesized or produced in a cellular system different from the cell from which it naturally originates will be substantially free from its naturally associated components. Accordingly, substantially pure polypeptides include those which naturally occur in eukaryotic organisms but are synthesized in *E. coli* or other prokaryotes.

By "substantially pure nucleic acid" is meant nucleic acid that is free of the genes which, in the naturally-occurring genome of the organism from which the nucleic acid of the invention is derived, flank the nucleic acid. The term therefore includes, for example, a recombinant nucleic acid that is incorporated into a vector; into an autonomously replicating plasmid or virus; into the genomic nucleic acid of a prokaryote or a eukaryote cell; or that exists as a separate molecule (e.g., a cDNA or a genomic or cDNA fragment produced by PCR or restriction endonuclease digestion) independent of other sequences. It also includes a recombinant nucleic acid that is part of a hybrid gene encoding additional polypeptide sequence.

The invention features plants that are resistant to pathogens and method for their production. Other features and advantages of the invention will be apparent from the following detailed description, and from the claims.

DESCRIPTION OF THE DRAWINGS

(FIG. 3A) *Elsinoe ampelina*, (FIG. 3B) *Fusarium oxysporium* isolated from watermelon.

FIG. 9 is a schematic illustration showing the nucleotide and amino acid sequence of the 33 kDa protein.

FIG. 11 is a schematic illustration showing a comparison of the amino terminal amino acid residues a 9 kDa protein from ECP of heart stage somatic embryos. This protein had high homology with several nsLTP: *Vitis* nsLTP P4 (SP accession no. P80274) (SEQ ID NO:7), *Vitis* nsLTP (Salzman et al., Plant Physiol 117:465–472, 1998) (SEQ ID NO:8), *Sorghum* nsLTP (SP accession no. Q43194) (SEQ ID NO:9), rice nsLTP (SP accession no. P23096) (SEQ ID NO:10). The consensus amino acid sequence (SEQ ID NO:11) is also shown. X denotes unidentified amino acid residue.

FIG. 12 is a schematic illustration showing a comparison of the amino terminal amino acid residues a 22 kDa protein from ECP of heart stage somatic embryos. This protein had high homology with several TLPs: Vvtl 1 (SP accession no. O04708) (SEQ ID NO:12) of, Tobacco TLP-E22 (accession no. P13046) (SEQ ID NO:13), Tobacco TLP-E2 (accession no. P07052) (SEQ ID NO:14), Vvosm (accession no. Y10992) (SEQ ID NO:15), and grape osmotin (GO; Salzman et al., supra) (SEQ ID NO:16). The consensus amino acid sequence (SEQ ID NO:17) is also shown. X denotes unidentified amino acid residue.

FIG. 13 is a schematic illustration showing a comparison of the amino terminal amino acid residues of the two ~22 kDa proteins from regenerated, in vitro selected plants (SEQ ID NOs:18 and 19). X denotes unidentified amino acid residue.

DETAILED DESCRIPTION OF THE INVENTION

Figure 1A:
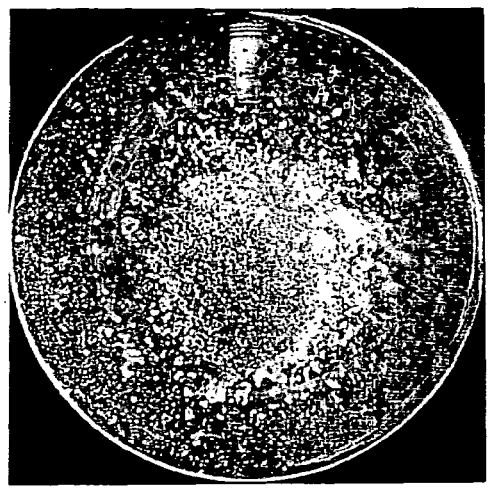
FIG. 1A is a photograph of a plant culture plate showing the embryogenic mass of 'Chardonnay' obtained from a liquid culture medium. This photograph was taken approximately ten weeks after the initiation of a liquid cell culture.

We have developed a method for growing perennial grape embryogenic cultures that is useful for the regeneration of grape plants. The unique germplasm resulting from our culture system has been observed to produce grape plants with an enhanced ability to recreate embryogenic cultures. Furthermore, we have developed a process for growing large quantities of somatic grape embryos from such perennial embryogenic cultures in a relatively short period using a liquid suspension culture. The culture method is useful, for example, for selecting somatic grape embryos capable of surviving in the presence of a pathogen. We have discovered that plants derived from these somatic embryos are also more resistant to pathogens. The plants of the invention are likely to have resistance to many pathogens. The "Compendium of Grape Diseases" (APS Press (1988) R. C. Pearson & A. C. Goheen, Eds.; hereby incorporated by reference) describes a wide variety of grape plant diseases and the pathogens that cause them. These include, without limitation, *botrytis* bunch rot and blight (*Botrytis cinerea*); black rot (*Guignardia bodwelli*); *phomopsis* cane and leaf spot (*Phomopsis viticola*); anthracnose (*Elsinoe ampelina*); bitter rot (*Greeneria uvicola*); white rot (*Coniella diplodiella*); ripe rot (*Colletotrichum gloeosporioides*); macrophoma rot (*Botryosphavria dothidea*); angular leaf spot (*Mycosphaerella nagulata*); diplodia cane dieback and bunch rot (*Diplodia natelensis*); rust (*Physopella ampelopsidis*); leaf blight (*Pseudocerospora vitis*); leaf blotch (*Brioisia ampelaphaga*); zonate leaf spot (*Cristulariella moricola*); septoria leaf spot (*Septoria* spp.); eutypa dieback (*Eutypa lata*); black dead arm (*Botryosphaeria steuensil*); *phymatotrichum* root rot (*Phymatotrichum omnivorum*); verticillium wilt (*Verticillium dahliae*); dematophora root rot; (*Dematophora necatrix*); phytophthora crown and root rot (*Phytophthora* spp.); crown gall (*Agrobacterium* spp.); bacteria blight (*Xanthomas ampelina*); Pierce's disease (*Xylella fastidiosa*); flavescence dorée; and bois noir and vergilbungskrankheit, and other grapevine yellows.

The regeneration methods described herein have been used for the successful regeneration by somatic embryogenesis of a variety of grapevine rootstock and scion cultivars, including Autumn Seedless, Blanc du Bois, Cabernet Franc, Cabernet Sauvignon, Chardonnay (e.g., CH 01 and CH 02), Dolcetto, Merlot, Pinot Noir (e.g., PN and PN Dijon), Semillon, White Riesling, Lambrusco, Stover, Thompson Seedless, Niagrara Seedless, Seval Blanc, Zinfindel, *Vitis rupestris* St. George, *Vitis rotundifolia* Carlos, *Vitis rotundifolia* Dixie, *Vitis rotundifolia* Fry, and *Vitis rotundifolia* Welder. The methods of the invention are generally applicable for a variety of grape plants (for example, *Vitis* spp., *Vitis* spp. hybrids, and all members of the subgenera *Euvitis* and *Muscadinia*), including scion or rootstock cultivars. Exemplary scion cultivars include, without limitation, those which are referred to as table or raisin grapes Alden, Almeria, Anab-E-Shahi, Autumn Black, Beauty Seedless, Black Corinth, Black Damascus, Black Malvoisie, Black Prince, Blackrose, Bronx Seedless, Burgrave, Calmeria, Campbell Early, Canner, Cardinal, Catawba, Christmas, Concord, Dattier, Delight, Diamond, Dizmar, Duchess, Early Muscat, Emerald Seedless, Emperor, Exotic, Ferdinand de Lesseps, Fiesta, Flame seedless, Flame Tokay, Gasconade, Gold, Himrod, Hunisa, Hussiene, Isabella, Italia, July Muscat, Khandahar, Katta, Kourgane, Kishmishi, Loose Perlette, Malaga, Monukka, Muscat of Alexandria, Muscat Flame, Muscat Hamburg, New York Muscat, Niabell, Niagara, Olivette blanche, Ontario, Pierce, Queen, Red Malaga, Ribier, Rish Baba, Romulus, Ruby Seedless, Schuyler, Seneca, Suavis (IP 365), Thompson seedless, and Thomuscat. They also include those used in wine production, such as Aleatico, Alicante Bouschet, Aligote, Alvarelhao, Aramon, Baco blanc (22A), Burger, Cabernet franc, Cabernet, Sauvignon, Calzin, Carignane, Charbono, Chardonnay (e.g., CH 01, CH 02, CH Dijon), Chasselas dore, Chenin blanc, Clairette blanche, Early Burgundy, Emerald Riesling, Feher Szagos, Fernao Pires, Flora, French Colombard, Fresia, Furmint, Gamay, Gewurztraminer, Grand noir, Gray Riesling, Green Hungarian, Green Veltliner, Grenache, Grillo, Helena, Inzolia, Lagrein, Lambrusco de Salamino, Malbec, Malvasia bianca, Mataro, Melon, Merlot, Meunier, Mission, Montua de Pilas, Muscadelle du Bordelais, Muscat blanc, Muscat Ottonel, Muscat Saint-Vallier, Nebbiolo, Nebbiolo fino, Nebbiolo Lampia, Orange Muscat, Palomino, Pedro Ximenes, Petit Bouschet, Petite Sirah, Peverella, Pinot noir, Pinot Saint-George, Primitivo di Gioa, Red Veltliner, Refosco, Rkatsiteli, Royalty, Rubired, Ruby Cabernet, Saint-Emilion, Saint Macaire, Salvador, Sangiovese, Sauvignon blanc, Sauvignon gris, Sauvignon vert, Scarlet, Seibel 5279, Seibel 9110, Seibel 13053, Semillon, Servant, Shiraz, Souzao, Sultana Crimson, Sylvaner, Tannat, Teroldico, Tinta Madeira, Tinto cao, Touriga, Traminer, Trebbiano Toscano, Trousseau, Valdepenas, Viognier, Walschriesling, White Riesling, and Zinfandel. Rootstock cultivars include Couderc 1202, Couderc 1613, Couderc 1616, Couderc 3309 (*Vitis riparia* X *rupestris*), Dog Ridge, Foex 33 EM, Freedom, Ganzin 1 (A×R #1), Harmony, Kober 5BB, LN33, Millardet & de Grasset 41B (*Vitis vinifera* X *berlandieri*), Millardet & de Grasset 420A, Millardet & de Grasset 101-14 (*Vitis riparia* X *rupestris*), Oppenheim 4 ($SO_4$), Paulsen 775, Paulsen 1045, Paulsen 1103, Richter 99, Richter 110, Riparia Gloire, Ruggeri 225, Saint-George, Salt Creek, Teleki 5A, *Vitis rupestris* Constantia, *Vitis californa*, and *Vitis girdiana, Vitis rotundifolia*, *Vitis rotundifolia* Carlos, Teleki 5C (*Vitis berlandieri* X *riparia*), 5BB Teleki (selection Kober, *Vitis berlandieri* X *riparia*), $SO_4$ (*Vitis berlandieri* X *rupestris*), and 039-16 (*Vitis vinifera* X *Muscadinia*).

Using plant tissue culture methods described herein, we have also developed in vitro selection methods which enable those skilled in the art to develop pathogen-resistant grapevines. One such application is the selection of mutations in grape cell cultures. In this application, cells that are resistant or susceptible to a particular condition are selected based on increased or selective growth. The cells can further be exposed to a mutagen that results in changes in the DNA of the exposed cells. The mutagenized DNA can then be identified using standard techniques.

A second, related application is the selection of pathogen-resistant cells. Cells are cultured in the presence of a phytotoxin from a plant pathogen. Cells that show resistance can then be used to regenerate a pathogen-resistant plant.

A third application is the transfer of genetic information into grape cells. The genetic information can include nucleic acid sequence encoding a selectable marker. Culturing cells in the presence of the selective pressure (e.g., in the presence of filtrate from a culture of *E. ampelina* at a concentration that kills cells not expressing a nucleic acid of the invention, such as SEQ ID NO: 6, but does not kill cells that are expressing the nucleic acid) results in the proliferation or survival only of the cells that have the desired genetic information. Those in the art will recognize that determination of the concentration of filtrate or related compounds may be determined by performing a standard dose-response assay.

There now follows a description for each of the aforementioned methods. These examples are provided for the purpose of illustrating the invention, and should not be construed as limiting.

EXAMPLE 1

Perennial Grape Embryonic Culture System

The following method has proven effective for the production of perennial embryogenic grape cultures, and for the regeneration of grapevine by somatic embryogenesis.

Explant Tissue and Culture Initiation

In the culture initiation step, explant material was collected from the field, greenhouse, or in vitro shoot micropropagation cultures of grapevine and placed into in vitro culture. This explant material was typically collected from leaves, anthers, or tendrils, but is also obtained from other vegetative or reproductive tissues of grapevine. Once collected, the explant tissue, if desired, was surfaced sterilized according to standard methods, and then placed on a suitable solid culture initiation medium in a petri plate.

Any of a number of well known media, e.g., Murashige and Skoog (MS) and Nitsch's medium, may be used. Such media typically include inorganic salts, vitamins, micronutrients, a nitrogen source, and a carbon source such as sucrose, maltose, glucose, glycerol, inositol, and the like. For example, sucrose may be added at a concentration of between about 1 g/L to about 200 g/L; and preferably at a concentration of between about 30 g/L to about 90 g/L. Moreover, the composition of such plant tissue culture media may be modified to optimize the growth of the particular plant cell employed. For example, the culture initiation medium may be prepared from any of the basal media found Table 1.

TABLE 1

COMPOSITION OF MEDIA COMMONLY USED IN THE EXAMPLES

| Component (mg/L unless otherwise specified) | MS | Modified MS | Nitsch |
|---|---|---|---|
| $KNO_3$ | 1900.0 | 3033.3 | 950.0 |
| $NH_4NO_3$ | 1650.0 | — | 720.0 |
| $NH_4Cl$ | — | 363.7 | — |
| $MgSO_4 \cdot 7H_2O$ | 370.0 | 370.0 | 185.0 |
| $CaCl_2$ | 440.0 | 440.0 | 166.0 |
| $KH_2PO_4$ | 170.0 | 170.0 | 68.0 |
| $Na_2EDTA$ | 37.23 | 37.23 | 37.3 |
| $FeSO_4 \cdot 7H_2O$ | 27.95 | 27.95 | 27.95 |
| $MnSO_4 \cdot H_2O$ | 16.9 | 16.9 | 18.9 |
| KI | 0.83 | 0.83 | |
| $H_3BO_3$ | 6.2 | 6.2 | 10.0 |
| $ZnSO_4 \cdot 7H_2O$ | 8.6 | 8.6 | 10.0 |
| $Na_2MoO_4 \cdot 2H_2O$ | 0.25 | 0.25 | 0.25 |
| $CuSO_4 \cdot 5H_2O$ | 0.025 | 0.025 | 0.025 |
| $CoCl_2 \cdot 6H_2O$ | 0.025 | 0.025 | 0.025 |
| Glycine | 2.0 | 2.0 | — |
| Nicotinic acid | 0.5 | 0.5 | 1.0 |
| Pyridoxin HCl | 0.5 | 0.5 | 1.0 |
| Thiamine HCl | 0.1 | 0.1 | 1.0 |
| Inositol | 0.1 g/L | 1.0 g/L | 0.1 g/L |
| Sucrose | 30.0 g/L; 60.0 g/L | 30.0 g/L; 60.0 g/L; 90.0 g/L | 20.0 g/L |
| Activated Charcoal | — | 0.5 g/L; 1.0 g/L, 2.0 g/L | — |
| Agar | 7.0 g/L | 7.0 g/L | 8.0 g/L |
| pH | 5.5 | 5.5 | 5.5 |

If desired, the initiation medium may contain an auxin or a mixture of auxins at a concentration of about 0.01 mg/L to about 100 mg/L, depending on the cultivar of interest, which is effective for inducing the production of embryogenic cells or embryogenic cell masses on the explant tissue. For example, explant tissue can be maintained on an agar-solidified Nitsch's-type medium supplemented with, for example, between about 0.01 mg/L and about 10 mg/L of 2,4-D, and preferably between about 0.5 mg/L and about 3.0 mg/L of 2,4-D. 2,4-D is just one example of an auxin which is useful in the methods of the invention. Other auxins include, for example, NAA, NOA, IAA, dicamba, and picloram. Additionally, if desired, other plant growth regulators may be included in the medium at standard concentrations. For example, cytokinins (e.g., a naturally-occurring or synthetic cytokinin, such as BA or zeatin), if present, may be used at a concentration of from about 0.01 mg/L to about 10 mg/L, and preferably about 0.3 mg/L, depending on the cultivar of interest. In some instances, other classes of growth regulators, such as ABA or GA, may be included at appropriate standard concentrations. For example, ABA may be added at a concentration of about 0.5 mg/L to about 20 mg/L, and preferably at a concentration of about 5 mg/L; and GA may be added at a concentration of about 0.1 mg/L to about 30 mg/L, and preferably at a concentration of about 5 mg/L. The addition of plant growth regulators at this stage is not necessary for the induction of embryogenesis. Additionally, the initiation medium may also include activated charcoal (0.1–2.0 g/L) or a similar adsorbent known to those in the art.

Culturing of explant tissue during this stage is preferably carried out in the dark at 22–30° C., although it may also be carried out under very low light conditions, or in full light. After approximately one to four weeks in culture, explant tissue cultures are then placed in full light with a 16 hr photoperiod. Cultures are scanned weekly for the presence of emerging embryogenic cells or embryogenic cell masses. Embryogenic cells or cell masses are identified based on morphology. Embryogenic cell masses, in general, tend to be white to pale yellow in color, and are often hyaline. They may be recognized from a very early, small stage (10–20 cell aggregates), based upon their color and friable, granular appearance. Embryogenic cultures are also identified by their compact nature with cells that are rich in cytoplasm (as seen under the microscope). The embryogenic cultures appear at varying frequencies depending on a multitude of factors including, but not limited to, genotype, nature and type of explant, medium composition, and season of harvest. Careful visual selection to ensure transfer of appropriate embryo-like structures is required for culture maintenance. Once identified, embryogenic cells or cell masses are then transferred to culture maintenance medium, as described herein.

Culture Maintenance

Embryogenic cells or embryogenic cell masses are carefully removed and transferred to a culture maintenance medium. Again, any of a number of well known media, e.g., MS and Nitsch's medium, may be used. Although not generally required, plant growth regulators may be added as described above.

In general, embryogenic tissue can be maintained by subculturing at regular intervals (e.g., every one to four weeks, or every four to eight weeks) to new maintenance medium, as described herein. Alternatively, embryogenic tissue can be placed in a liquid culture medium (e.g., MS, B-5, or Nitsch) and grown as a liquid embryogenic suspension as described herein. Embryogenic cell masses are grown to increase embryogenic cell biomass as required by division of expanding cultures during transfer. The cultures can be prompted to develop toward increasing embryogenesis or toward less embryogenesis and more unorganized embryogenic cell growth by repeated manipulation of the culture, which includes careful selection of embryogenic cells and cell masses during transfer. Repeated transfer of embyogenic cells or cell masses has not only been found to enrich the growth of embryogenic tissue, but also to facilitate the process of somatic embryogensis. The cultures are perennial in that they typically persist for over two years.

A key component of the present approach involves the careful selection of embryogenic cells from explanted tissue, followed by recurrent selection and subculturing of the selected embryogenic tissue. This material has not only been found to be useful in the regeneration of whole grape plants from somatic embryos, but has also been found to have a significantly increased capacity for embryogenesis, including the production of somatic embryos. By carrying out this procedure, the growth of embryogenic cells is enriched, speeding the process of somatic embryo formation and subsequent plant regeneration.

The explant material taken from plants that were grown from somatic embryos was observed to exhibit an enhanced embryogenic potential, when compared to explant material taken from clonal explant tissue which had not been cultured for the production of embryogenic cells. This increase in embryogenic potential was observed to increase after two or more successive initiation, culture and plant regeneration cycles (e.g., clonal plant-->explant-->embryogenic culture initiation-->somatic embryo-->somatic embryo-derived plant-->explant). It is not necessary to use a somatic embryo-derived plant as the source of the explant; somatic embryos or even embryogenic cultures that have been transferred to new medium will also produce new somatic embryos with increased embryogenic potential. Such explant material is conveniently maintained as in vitro axillary shoot cultures, which serves as the source for vegetative explants; however, other methods of plant maintenance are also acceptable.

Germination and Plantlet Growth

Somatic embryos obtained from the above-described cultures are subsequently germinated into grape plantlets according to standard methods. For example, somatic embryos are placed on the surface of a germination medium (e.g., MS medium) in sterile petri plates. The cultures containing the embryos are incubated in a growth chamber under lighted conditions (16 hr photoperiod). During germination the root emerges and the epicotyl begins to grow. When grape plantlets that are grown on germination medium reach sufficient size (1 cm, with at least two leaves), they can be removed from the culture dishes and planted in a sterilized potting mixture. Plantlets are typically transferred into nursery containers in a soiless potting mix (e.g., Vermiculite, Perlite, or ProMix™, V. J. Growers, Apopka, Fla.). If desired, plantlets can be placed in a growth chamber or in a greenhouse moisture chamber and incubated under high humidity conditions (90% humidity) for plantlet growth and acclimatization. Subsequently, acclimatized plantlets can be transferred outdoors to a vineyard or to a greenhouse.

In one example, we describe the production of an embryogenic perennial culture of *Vitis vinifera* cv. 'Thompson Seedless.' Mother plant-derived cultures were obtained from a leaf that was surface-disinfected and inoculated onto culture initiation medium described by Nitsch (1968) and modified by Gray D. J. ("Somatic Embryogenesis in Grape." In: *Somatic embryogenesis in woody perennials*, Vol. 2, Gupta P. K., Jain S. M., and Newton R. J. (Eds.), Kluwer Academic, Dordrecht, The Netherlands, pp. 191–217, 1995). This medium contained about 1.1 mg/L of 2,4-D and about 0.05 mg/L of BA. After explanting the tissue, the culture vessels were incubated in complete darkness for six weeks. Most of the explanted tissue was observed to form a mass of undifferentiated, highly vacuolated cells within this six week period. Embryogenic cultures, identified by their compact nature and the presence of cells that were rich in cytoplasm, were repeatedly subcultured. The resulting culture was obtained by the selection method described above, followed by subculturing (for about 6 weeks) until enough embryogenic culture was available. A somatic embryo originally obtained from the mother plant (i.e., $1^{st}$ generation embryo) was germinated, and its shoot tip used to create an in vitro micropropagation culture. Leaves from the plant derived from that culture were then used to produce a new embryogenic culture ($2^{nd}$ generation). A somatic embryo obtained from that culture was similarly used to create the third generation. The embryogenic response of *Vitis vinifera* cv. 'Thompson Seedless' from in vitro micropropagation culture-derived leaves is presented in Table 2. These results show the comparison of leaves from potted mother plant-derived cultures with leaves from plants derived from cultures obtained from third-generation germinated somatic embryos.

TABLE 2

| Culture derivation | No. leaves cultured | No. embryogenic cultures | % response per leaf |
| --- | --- | --- | --- |
| Mother plant | 195 | 0* | 0 |
| $3^{rd}$ generation somatic embryo | 200 | 14 | 7# |

*Other experiments have yielded one embryogenic culture.
The percent response per leaf has been found to be has high as 30%.

In addition, perennial embryogenic cultures from other grapevines have also been produced using the methods described herein, including *Vitis longii, Vitis rotundifolia* (cv. Carlo and Dixie), *Vitis rupestris, Vitis vinifera* (cv. Autumn Seedless, Cabernet Sauvignon, Cabernet Franc, Chardonnay, Dolcetto, Gamay Beaujolais, Lambrusco, Pinot Noir, Semillon, Tokay, White Riesling, Zinfindel, and the like), and several *Vitis* hybrids (cv. Blanc du Bois, Niagara Seedless, Seyval Blanc, Stover, Southern Home and the like).

EXAMPLE 2

Production of Highly Embryogenic Grape Cells Using Liquid Suspension or Solid Cultures A method has also been developed for the production of large quantities of grapevine somatic embryos using either a liquid cell suspension culture or a solid culture system. These methods are particulary useful for producing highly embryogenic cells that are capable of regenerating into whole plants. Below, a simple protocol for efficient somatic embryogenesis of grapevine using either a liquid cell suspension culture or a solid culture system is presented.

In general, the method includes a multistage culturing process typically involving (i) culture initiation; (ii) identification and isolation of embryogenic cells or embryogenic cell masses; (iii) production of perennial embryogenic cultures; and (iv) concentration of highly embryogenic cell clusters. The method involves the following steps.

Explant tissue is placed on a suitable culture initiation medium, as is described herein. After approximately six weeks on culture initiation medium, embryogenic cells and embryogenic cell masses are identified. Once identified, embryogenic cultures, which may be less than 1 mm in diameter, are isolated and cultured on fresh initiation medium to encourage growth, as described herein. Subculturing of the embryogenic cultures typically results in the formation of somatic embryos. Embryogenic cultures and early stage somatic embryos obtained from these cultures are then further cultured in a suitable liquid plant growth medium. For example, the plant tissue culture nutrient media, consisting B-5 medium (Gamborg et al., Exp. Cell. Res. 50:151–158, 1968; Sigma Chemicals, St. Louis, Mo.), that has been modified as described by DeWald et al. (J. Amer. Soc. Hort. Sci. 114:712–716, 1989) and Litz et al. ("Somatic embryogenesis in mango," 1995, supra). This modified medium consists of B-5 major salts, MS minor salts and vitamins, glutamine (about 400 mg/L), and sucrose or commercial table sugar (about 60 g/L). Before autoclaving, the pH of the medium is adjusted to about 5.8. Although 2,4-D (about 0.5–2.0 mg/L) is the preferred growth regulator used in this medium, other growth regulators, such as, for example, dicamba, picloram, NOA, or 2,4,5-trichlorophenoxy acetic acid, may be also used at appropriate concentrations, for example, those described above. Flasks containing the embryogenic cell cultures, somatic embryos, or both are subsequently incubated at about 26° C. on a rotary shaker at 125 rpm in darkness or diffuse light. The cultures are then subcultured as described herein, typically once every ten to fourteen days, but subculturing regimens may vary depending on the growth and proliferation of embryogenic cell clusters.

In about six to eight weeks, a fine cell suspension culture is produced, which consists of highly-vacuolated elongated cells (non-embryogenic cells), and also a lesser number of small, cytoplasm-rich, isodiametric cells (embryogenic cells). Once sufficient culture is produced, the differentiated embryos can be removed from the culture by sieving, and the differentiated embryos are discarded. Continued maintenance of the sieved embryogenic cell suspension culture in modified B-5 liquid medium, with periodic subcultures, has been found to increase the biomass of embryogenic cell clusters.

After approximately twelve to sixteen weeks, a large mass of highly concentrated embryogenic grape cells is typically observed. The time taken for the concentration of embryogenic cells or embryogenic cell masses may vary depending on several factors, including the cultivar, genotype, and culture conditions. Embryogenic cells at this stage are especially useful in virtually any type of genetic transformation method. These embryogenic cells can also be induced to differentiate into somatic embryos according to any standard method, e.g., by culturing the cells in modified B-5 liquid medium devoid of growth regulators for a period of about four to six weeks. Alternatively, the early stage somatic embryos may be plated in medium solidified by the addition of a suitable gelling agent such as gellan gum, agarose, agar, or any other similar agent, for further differentiation of somatic embryos in complete darkness. If desired, torpedo/cotyledonary-stage embryos can be individually subcultured on a standard maturation medium, e.g., a maturation medium consisting of MS nutrient formulations. Mature somatic embryos are then transferred to a growth chamber for germination, and regeneration to plants in an appropriate container. The frequency of somatic embryo formation using this procedure is typically high.

There now follows a description of the results for the production of embryogenic cells and cell masses obtained from a liquid suspension and solid cultures of 'Thompson Seedless' and two different clones of 'Chardonnay,' CH 01 and CH 02.

Asynchronous somatic embryos of *Vitis vinifera* cv. 'Thompson Seedless' and 'Chardonnay' CH 01 and CH 02 obtained from perennial embryogenic tissue were further cultured in a liquid medium to produce a callus tissue suspension culture. After about fourteen days and following about two to three subcultures (a subculture was performed about every fourteen days), an amorphous, yellowish to creamy white colored callus was produced. As a result of the production of callus tissue, the liquid culture media in the tissue culture flask appeared as a dense suspension. Microscopic examination revealed that the callus cells were elongated and highly vacuolated, and exhibited no signs of embryogenic capacity. Amorphous callus continued to proliferate, even when the somatic embryos used to initiate the culture were removed from the culture.

After approximately six weeks in modified B-5 liquid medium, we observed the production of small clusters of cytoplasm-rich cells as white clumps (FIG. 1A). These embryogenic masses were observed to proliferate exponentially, and grew to the capacity of the flask in about ten to twelve weeks.

Continued maintenance of these embryogenic masses as a single unit (i.e., in one flask) is often detrimental, as the cultures have been found to deteriorate in quality, and eventually turn brown. Dividing these embryogenic cultures into smaller units during subculturing assists to proliferate and increase the biomass of the divided cultures. Among the two cultivars tested, both clones of 'Chardonnay' were found to be equally fast growing and outgrew 'Thompson Seedless.' While the embryogenic masses of 'Chardonnay' were creamy white to yellowish in color, those of 'Thompson Seedless' were dull white or brownish. In addition, 'Thompson Seedless' appeared to be more sensitive to culture density, as the cells were observed to turn dark if the culture density was not corrected. The preferred culture density was approximately 400 mg of embryogenic cells per 40 mL of liquid modified B5 medium in a 125 mL flask.

Somatic Embryo Production in Liquid Culture

Embryogenic masses were passed through a 960 micron nylon sieve and collected in a sterile beaker. Sieving of the embryogenic masses to initiate embryogenesis in liquid culture was found to serve two purposes. First, a fair degree of synchronization of embryo differentiation was obtained. Second, the formation of somatic embryo abnormalities during differentiation, such as fasciation or fusion, was reduced. After four to six weeks in liquid medium, small, white somatic embryos in the globular or early heart stage were observed. Sieving the cultures at this stage did not facilitate an increase in embryo differentiation.

After approximately eight weeks, somatic embryos were clearly visible, and a few embryos were found to have reached the cotyledonary stage of embryo development. Sieving the differentiated embryos and culturing them in a separate flask, however, facilitated faster differentiation, as well as synchronization of embryo devlopment.

Figure 1B:
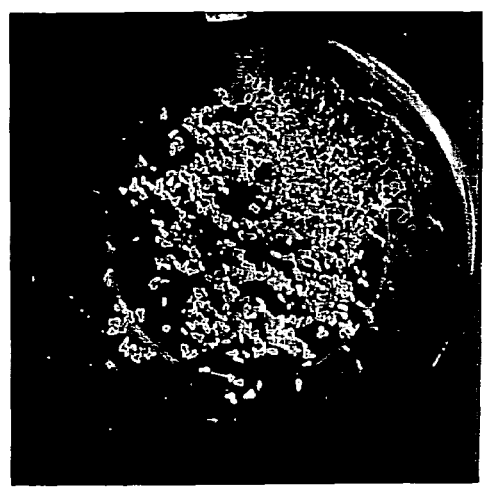
FIG. 1B is a photograph of a plant culture plate showing cotyledonary stage somatic embryos. This photograph was taken approximately twelve weeks after the initiation of embryo development.
Figure 1C:
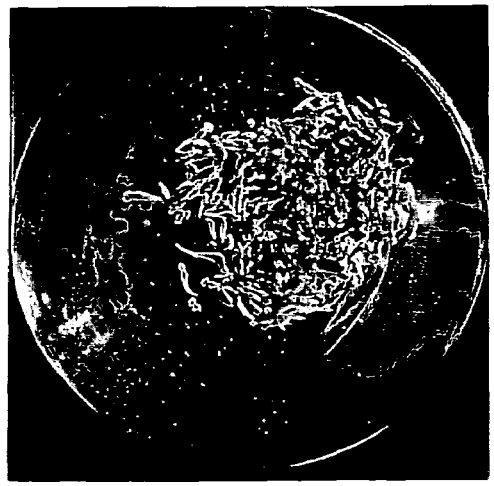
FIG. 1C is a photograph of a plant culture plate showing mature somatic embryos starting to precociously germinate in liquid culture. Note the elongation of roots in many embryos. This photograph was taken approximately twenty weeks after the initiation of embryo development.

Both 'Chardonnay' clones—CH 01 and CH 02—were found to readily differentiate into somatic embryos. Appropriate sieving and density adjustment (performed by culturing about 1000 mg of somatic embryos per 40 mL medium) ensured greater synchronization and singulation, as well as embryo differentiation (FIG. 1B). In approximately twelve to fourteen weeks after subculture in liquid embryogenesis medium, singulated somatic embryos started to turn green and radicles elongated, showing the onset of precocious germination (FIG. 1C).

Cultures of 'Thompson Seedless' initially were found not to advance beyond the heart stage in liquid culture. In addition, the embryos were found to be more clustered, often resulting in the formation of fused somatic embryos. Removal of the abnormal embryos and lowering the culture density by half resulted in normal somatic embryogenesis in liquid culture. These somatic embryos reached maturity in about fourteen to eighteen weeks.

Somatic Embryo Production in Solid Medium

Figure 1D:
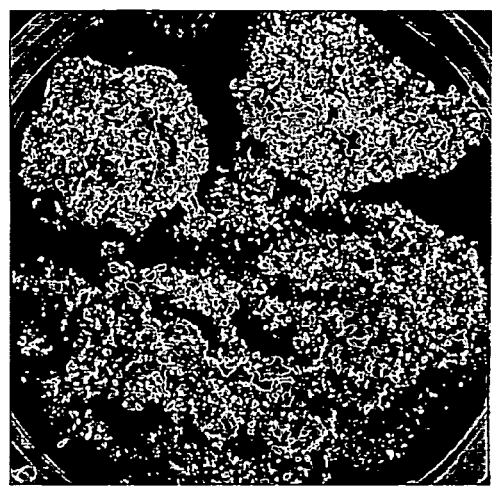
FIG. 1D is a photograph of a plant culture plate showing initial stages of somatic embryo differentiation in a solid medium after five weeks of culturing. These somatic embryos were obtained from embryogenic cell masses that were cultured in a liquid medium (from FIG. 1A).
Figure 1E:
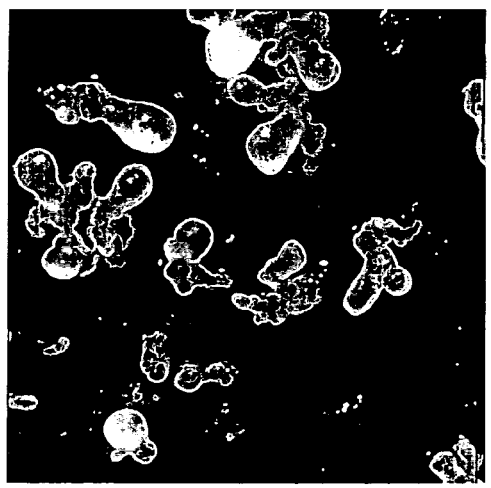
FIG. 1E is a photograph of a plant culture plate showing the early stages of somatic embryo development in a solid medium. Very early somatic embryos are hyaline and start turning opaque after a few days.
Figure 1F:
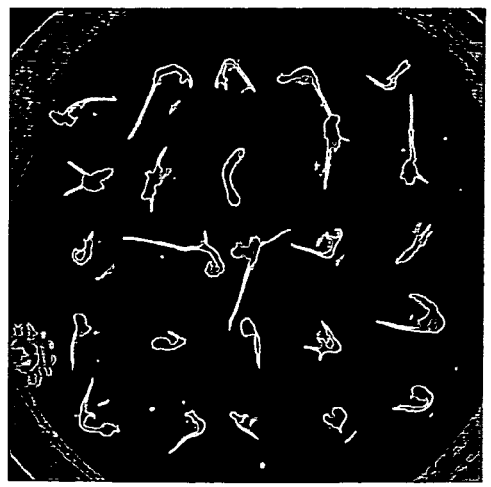
FIG. 1F is a photograph of a plant culture plate showing mature somatic embryos germinating on a MS basal medium with 3% sucrose.

Embryogenic cells or embryogenic cell masses obtained from liquid cultures were observed to differentiate into somatic embryos as early as three weeks after culture initiation. After four weeks of culture, microscopic examination also revealed the formation of globular and heart shaped somatic embryos on the callus tissue (FIG. 1D). The somatic embryos were hyaline, and resembled that of a hyperhydric state (FIG. 1E); however, the embryos continued to differentiate, and were found to develop into mature somatic embryos in another three to four weeks. These somatic embryos were observed to develop a suspensor (FIG. 1E). In addition, embryogenic cells were observed to develop into a mass of asynchronous somatic embryos.

One of the interesting observations from these experiments was that the majority of somatic embryos arose as individual units, and not as small clumps, although there were a few clumps of somatic embryos. In such cases, the number of somatic embryos ranged from six to ten in each clump, and these embryos were easily separated from the callus tissue. Embryos found in the cotyledonary stage were isolated on a weekly basis, and subcultured for maturation. Each clump of embryogenic mass continued producing somatic embryos for at least twelve weeks. Embryogenic cell masses tended to turn brown in solid medium, containing Gel-Gro (ICN Biochemicals), but this discoloration did not adversely affect culture viability. About four or five weeks later, clusters of somatic embryos started to appear on the surface of the brown embryogenic cells or embryogenic cell masses.

Somatic Embryo Maturation, Germination and Plant Regeneration

Three maturation media—mango maturation medium (Litz et al., 1995, supra); mango maturation medium solidified with agar (7 g/L); and MS basal medium with 3% sucrose—were studied to evaluate the ability to promote somatic embryo germination and plant regeneration. Our results indicated that a MS basal medium containing 3% sucrose was the most effective at promoting embryo maturation, germination, and plant regeneration, for both embryos derived from solid medium and for the precociously germinated embryos that were obtained from liquid medium cultures (FIG. 1D). Although there was good germination on mango maturation medium with agar, the quality of the regenerants was not as good as with MS salts with 3% sucrose. Embryos from the two systems studied (i.e., liquid and solid media) showed variation between themselves in germination and regeneration. Although embryos have precociously germinated in liquid cultures, continued germination in these cultures was not observed. On transfer to solid medium, however, the embryos were found to continue the germination process, and resulted in the formation of grape plants with a dense root system. Continued maintenance in liquid medium after radicle emergence lead to hyperhydricity and eventually plant regeneration was reduced from these embryos. Accordingly, it is preferred that the somatic embryos should be removed from the liquid as soon as they precociously germinate and transferred to solid medium.

Long-Term Preservation of Suspension-Derived Grapevine Somatic Embryos and Regeneration of Plants We have established a method for the long-term storage of somatic embryos. Mature somatic embryos from suspension cultures of 'Chardonnay' were blot-dried on sterile filter paper in a laminar-flow hood and then stored in sterile petri plates at 6° C. Samples were periodically drawn from these plates and germinated on MS medium with 3% sucrose. Germination (i.e., the emergence of roots from the somatic embryo) and plant regeneration were recorded. Table 3 shows the data from clone CH 02 after 22 months in storage, and Table 4 shows the data from clone CH 01 after 5 months in storage.

TABLE 3

| Trial Number | Number of Embryos | Number Germinated (Percent Germinated) | Number of Plants | Percent Yield |
|---|---|---|---|---|
| 1 | 87 | 81 (93.1) | 69 | 79.3 |
| 2 | 42 | 40 (95.2) | 35 | 83.3 |
| 3 | 41 | 41 (100.0) | 30 | 73.2 |
| Total | 170 | 162 (95.3) | 134 | 78.8 |

TABLE 4

| Trial Number | Number of Embryos | Number Germinated (Percent Germinated) | Number of Plants | Percent Yield |
|---|---|---|---|---|
| 1 | 15 | 15 (100.0) | 13 | 86.7 |
| 2 | 15 | 15 (100.0) | 13 | 86.7 |
| 3 | 15 | 13 (86.7) | 9 | 60.0 |
| 4 | 15 | 12 (80.0) | 7 | 46.7 |
| 5 | 15 | 13 (86.7) | 9 | 60.0 |
| 6 | 15 | 11 (73.3) | 9 | 60.0 |
| 7 | 15 | 15 (100.0) | 14 | 93.3 |
| 8 | 15 | 13 (86.7) | 9 | 60.0 |
| Total | 120 | 107 (89.2) | 83 | 69.2 |

Direct Seeding of Suspension Culture-Derived Grapevine Somatic Embryos

'Chardonnay' and 'Thompson Seedless' grapevine somatic embryos were produced from liquid cultures as described herein. Suspension-derived, mature somatic embryos were blot dried briefly in the laminar flow hood and germinated directly in Magenta vessels containing one of the following potting media: i) sand; ii) ProMix™ commercial potting mixture (CPM); or CPM overlaid with sand. Each vessel containing 20 mL of distilled water and the potting medium was sterilized by autoclaving for 30 min and cooled overnight prior to inoculating the somatic embryos. Three somatic embryos were placed in each vessel. Seeding was carried out under aseptic conditions and the containers were closed and incubated at 26° C. with a 16 hr photoperiod at 75 $\mu$mol s$^{-1}$ m$^{-2}$ light intensity. Results revealed that CPM overlaid with sand was ideal for plant development. Although sand promoted more germination, the resulting plants were chlorotic and their survival rate was poor. There was more contamination of somatic embryos on pure CPM. The present study offers scope for large-scale multiplication of grapes using suspension cultures and sets the platform for growing grape somatic embryos in bioreactors.

The experimental results described above were carried out using the following techniques.

Culture Initiation

Embryogenic cultures were initiated from anthers and ovaries of the cultivar "Chardonnay" (Clones CH 01 and CH 02), and from the leaves of the cultivar "Thompson Seedless" according to standard methods, e.g., those described herein. Somatic embryos of these cultures, initiated and maintained in modified MS medium, were used to initiate liquid cell suspension cultures. Typically these cultures are highly asynchronous in embryonic development and differentiation and, therefore, each inoculum consisted of somatic embryos at various stages of development.

Establishment of Liquid Cultures from Differentiated Somatic Embryos

The composition of the liquid medium was adapted from the medium described by Litz et al., supra as follows. Callus induction was achieved by the addition of 1 mg/L of 2,4-D in the medium. The pH of the medium was adjusted to about 5.8, and dispensed as 40 mL aliquots in 125 mL Erlenmeyer flasks. The flasks were tightly covered with heavy duty aluminum foil before autoclaving. After cooling, approximately one gram of the somatic embryos was transferred to the liquid medium using a sterilized spatula under aseptic conditions. The neck of the flask was sealed with Parafilm, and the cultures were then incubated in semi-darkness (diffused light) on a rotary shaker at about 120 rpm. The cultures were subcultured at least one time every two weeks.

Flasks containing the suspension cultures were removed from the orbital shaker and the cultures were allowed to settle for about 15 minutes. The supernatant was gently decanted into a sterile flask, leaving the embryogenic cells in a minimal volume (approximately 5 mL). Approximately 35 mL of fresh liquid medium was added to the embryogenic cells and swirled quickly. The entire contents of the flask were then transferred to a sterile 125 mL flask. This second flask, containing the embryogenic cells, was then sealed with Parafilm and returned to the orbital shaker.

The amorphous callus generated from the somatic embryos was collected as follows. The embryogenic suspension, including differentiated somatic embryos and callus, was allowed to settle in the flasks. About half of the supernatant medium was decanted, and the remainder was swirled and quickly filtered through a presterilized, nylon mesh (960 microns), placed over a 150 mL beaker. While the differentiated somatic embryos were retained in the mesh, the fine callus that passed through along with the liquid medium was collected in the beaker. The callus that was collected in the beaker was next filtered through a sterile, double-folded, Kimwipe placed over a sterile funnel. The amorphous callus that adhered to the Kimwipe was subsequently removed from the Kimwipe using a sterilized spatula, and resuspended in fresh liquid culture medium. Approximately 100 mg of the callus was suspended in each flask. These liquid cultures were subcultured as described herein approximately once every fourteen days in modified B-5 liquid medium containing 2,4-D.

Somatic Embryo Production in Suspension Culture

Embryogenic cells or cell masses that were initiated in liquid suspension cultures were sieved using a 960 micron sieve, and the finer fraction was harvested in liquid embryogenesis medium, under aseptic conditions. The medium composition was the same as that of the initiation medium; however, 2,4-D was omitted from the medium and about 0.05 mg/L of BA was added. After adjusting the pH to 5.8, the medium was dispensed as 40 mL aliquots in 125 mL Erlenmeyer flasks, covered with aluminum foil and autoclaved. Approximately 100 mg of callus was cultured in each flask. The cultures were maintained in semidarkness at 25° C. on a rotary shaker at 120 rpm, and subcultured once every 14 days. Sieving of cultures was done as necessary, in order to synchronize differentiated somatic embryos. Finer mesh sieves (e.g., 520 micron sieves), if necessary, may also be employed.

Germination of Somatic Embryos from Suspension Cultures and Regeneration

Greening somatic embryos having elongated radicles were sieved from the suspension cultures. Somatic embryos were individually picked and cultured. Three different media—mango maturation medium (Litz et al., supra), mango maturation medium solidified with agar (7 g/L) instead of Gel-Gro, and MS basal medium with 3% sucrose—were tested for germination and plant regeneration. Plant growth regulators were omitted from these media preparations. Twenty-five embryos were cultured in each standard petri plate, and eight plates of each medium was tested. After sealing with Parafilm, the cultures were incubated in a growth chamber under a 16 hour photoperiod. Plantlets with four true leaves were subsequently transferred to soil.

Somatic Embryo Production in Solid Medium

Embryogenic cells and embryogenic cell masses produced in suspension cultures were harvested as described above and then transferred to solid embryogenesis medium. The medium consisted of the same compounds as the liquid embryogenesis medium, and solidified with 2.0 g/L Gel-Gro or 7 g/L agar. Approximately 50 mg of callus was placed as a clump onto a medium-containing petri plate and each plate had two such clumps. After inoculating, the petri plates were sealed with Parafilm and incubated in complete darkness. Subculturing was performed after somatic embryo differentiation was observed. Somatic embryos produced from the embryogenic cells or embryogenic cell masses were counted on a weekly basis, starting from six weeks after culture. Embryos of cotyledonary stage were counted and subcultured for maturation.

Maturation and Germination of Somatic Embryos from Solid Medium

Mature somatic embryos that were approximately 5 mm in length were isolated from the asynchronous mass and cultured on maturation medium. Twenty-five mature somatic embryos were cultured in each standard petri plate on MS medium with 3% sucrose. The cultures were kept in the dark until they germinated. After elongation of radicle, they were transferred to light under a 16 hour photoperiod. Plantlets with at least four true leaves were subsequently transferred to soil.

EXAMPLE 3

Selection of Disease Resistant Embryogenic Cells and Plants of Grapevine

The perennial grape embryogenic cultures of the invention can be used for the selection or screening for grape cells having resistance to toxic substances, such as those present in a filtrate produced by a fungal culture. Such pathogens include, without limitation, bacteria and fungi. Plant diseases generally caused by these pathogens are described in Chapters 11–16 of Agrios, *Plant Pathology*, 3rd ed., Academic Press, Inc., New York, 1988, hereby incorporated by reference. The "Compendium of Grape Diseases" (APS Press (1988) R. C. Pearson & A. C. Goheen, Eds.) describes diseases that affect grape plants. Examples of bacterial pathogens include, without limitation, *Agrobacterium vitis, Agrobacterium tumefaciens, Xylella fastidosa*, and *Xanthomonas ampelina*. Examples of fungal pathogens include, without limitation, *Plasmopara viticola, Botrytis cinerea, Guignardia bidwellii, Phomophsis viticola, Elsinoë ampelina, Eutypa lata, Armillaria mellea*, and *Verticllium dahliae*. Others are described herein.

By exposing embryogenic cultures to a phytotoxin (e.g., crude culture filtrate or a purified phytotoxin obtained from a plant pathogen), resistant grape cells can be selected and propagated. Grape cells that survive the selection pressure are expected to resist not only the selecting toxin, but also the original microbe that produces the toxin. Moreover, due to the dynamics of the selection process, induced resistance may also function against an array of disease-causing organisms beyond the original microbe used for selection. Because the selection is carried out at the cellular level, it is likely that grape plants regenerated from the cells will show the selected characteristic. In particular, this system allows one skilled in the art to select or screen for the desired characteristic from among thousands of cells in a single culture flask or petri plate.

EXAMPLE 4

Methods for Selecting Pathogen-Resistant Somatic Embryos and Producing Plants

Various microbes attack grapevine and cause a number of diseases. These diseases include fungal diseases of leaves and fruits (such as black rot and anthracnose), fungal diseases of the vascular system and roots (such as Esca, Black Measles, Black Dead Arm, and *Eutypa* dieback) and bacterial diseases (such as crown gall and Pierce's disease).

One disease affecting grapevine is anthracnose, also known as bird's eye spot disease, which is caused by the fungus, *E. ampelina*. Under favorable conditions, this fungus attacks almost all the aerial parts of the grapevine, including fruits, causing extensive damage to the crop. Anthracnose causes the appearance of circular lesions with brown or black margins and round or angular edges on the grapevine plant. The center of the lesions becomes grayish white and eventually dries up and falls off, leaving a 'shot-hole' appearance. The disease especially affects young leaves, preventing normal development. New shoots are also affected and acquire an obvious, burnt appearance. Fruit clusters are also susceptible to fungal infection throughout their development; lesions on the berries extend into the pulp, often inducing cracking.

Preparation of Phytotoxin

An *E. ampelina* culture filtrate having toxic activity was prepared as follows. Full-strength Czapekk-Dox broth medium (Fisher Scientific, Springfield, N.J.) was prepared by dissolving the required amount of the broth mixture in deionized (DI) water. The medium was dispensed as 50 mL aliquots in 125 mL Erlenmeyer flasks. After autoclaving and cooling, 100 μL of a *E. ampelina* spore suspension was added to each flask (Day 1); the flask was then incubated in a rotary shaker at 25° C. at 120 rpm for one week in the dark. After one week, the contents in each flask were transferred to 100 mL of full strength Czapek-Dox in a 250 mL Erlenmeyer flask and the incubation was continued for two more weeks. At the end of this period (i.e., three weeks from Day 1), the fungal culture filtrate was collected by filtering the contents of each flask through a sterile, multi-layer cheese cloth. The crude culture filtrate was stored at −4° C. until further use.

Prior to addition to the culture media for in vitro selection, the frozen culture filtrate was thawed (without heating) at room temperature, pH adjusted to 5.8, and filter-sterilized through a 0.2 micron filter (Nalgene, Rochester, N.Y.). This filter-sterilized pathogen filtrate was found to retain its toxic activity, as determined by its ability to cause grape plant cell death.

Selection

The *E. ampelina* culture filtrate was next added to liquid suspension cultures of *V. vinifera* cv. 'Chardonnay' embryogenic cells and embryogenic cell masses in modified B-5 medium to select cells having resistance to the toxic fungal culture filtrate. The grape embryogenic cells and embryogenic cell masses were grown as described above; however, in this in vitro selection, the medium in which the cells were grown was supplemented with known volumes of *E. ampelina* culture filtrate. Appropriate dilutions of pathogen filtrate were determined by examining the toxicity of the filtrate using serial dilution analysis. These experiments demonstrated that a 40% (v/v) culture filtrate was useful for in vitro selection.

Cultures of 'Chardonnay' embryogenic cells and embryogenic cell masses were maintained in liquid medium containing 40% (v/v) fungal culture filtrate at about 26° C. on a rotary shaker (125 rpm) in diffuse light. Subculturing was done once every ten days; during each subculture, filter-sterilized culture filtrate was used to dilute the medium. Selection with culture filtrate was continued for four or five cycles (each cycle=ten days) of subculture. While most of the embryogenic cells died, a very few cells, often less than 1%, survived the selection pressure. Resistant culture lines were established by withdrawing the selection pressure after four or five cycles and letting the surviving cells grow in modified B-5 medium devoid of culture filtrate. These resistant lines were proliferated, and somatic embryo were produced using the methods described herein.

Embryogenic cell cultures obtained from the selection process were subsequently tested for resistance to *E. ampelina* using a number of in vitro bioassays. We first analyzed whether the resistant grapevine lines were producing an activity that could inhibit the growth of the fungus. To this end, the culture medium (i.e., conditioned culture medium) from a resistant culture line was tested for an inhibitory activity against the fungus. Conditioned media was collected from different cell cultures having resistance to *E. ampelina*, and used in several concentrations to prepare fungal growth media. An actively growing mycelial colony was placed in the center of a petri plate containing a fungal growth medium prepared with or without (control) conditioned medium from a resistant grapevine culture line and incubated under standard conditions. The results of these experiments showed that the growth of the fungus was inhibited by a fungal growth medium containing 25% or more of the conditioned medium.

To further demonstrate the presence of anti-fungal activity in resistant grapevine cultures, resistant lines, as well as control lines, were placed in solid plant growth medium in six and twelve o'clock positions in petri plates, and incubated in darkness for four weeks. After this period, a plug of mycelium from an actively growing *E. ampelina* colony was placed in the center of the petri plates and incubated under standard conditions. The fungus was observed to grow rapidly and infect the control cultures. Conversely, fungal growth was inhibited on the plates containing grape cell cultures having resistance to the *E. ampelina* culture filtrate. Hyphae did not grow freely through the medium in plates containing these resistant cultures, as compared to fungal hyphae growth through the medium in plates containing control (i.e., non-resistant) cultures. A thick mat of mycelium, as seen in the plates containing control cultures, was never formed in the plates containing the *E. ampelina* resistant cultures. This capacity of the resistant cultures to inhibit the growth of *E. ampelina* was retained nine months after selection, demonstrating that the genetic changes in the resistant cultures were stable.

In addition, the grapevine cultures that were resistant to *E. ampelina* were tested for resistance to a second fungal pathogen, *Fusarium* (*F.*) *oxysporum*. Resistant lines, as well as control lines, were placed in solid plant growth medium in six and twelve o'clock positions in petri plates, and incubated in darkness for four weeks. After this period, a plug of mycelium from an actively growing *F. oxysporum* colony was placed in the center of the petri plates and incubated at room temperature under a 16 hour photoperiod. The fungus was observed to grow rapidly and infect the control cultures. Conversely, growth of *F. oxysporum* was inhibited on the plates containing grape cell cultures having resistance to the *E. ampelina* culture filtrate. Hyphae did not grow freely through the medium in plates containing these resistant cultures, as compared to fungal hyphae growth through the medium in plates containing control (i.e., non-resistant) cultures. A thick mat of *Fusarium* mycelia, as seen in the plates containing control cultures, was never formed in the plates containing the *E. ampelina* resistant cultures. This experiment demonstrated that the resistant grapevine cultures were not only resistant to *E. ampelina*, but were also resistant to *F. oxysporum.*

Further analysis was made to determine if the fungal-resistant grapevine cultures could give rise to somatic embryos that were also resistant to *E. ampelina*. Somatic embryos derived from resistant cultures and control cultures were grown either in medium containing 40% (v/v) of fungal culture filtrate or in control medium containing no fungal culture filtrate. While somatic embryos derived from the resistant cultures formed and germinated normally in both the fungal culture filtrate-containing medium and control medium, somatic embryos derived from control cultures turned necrotic and eventually died in the fungal culture filtrate-containing medium, but did not die in the control medium. The necrosis of the controls in the fungal culture filtrate-containing medium was rapid enough to turn the control somatic embryos dark within seventy-two hours of culture initiation. The results from these experiments demonstrated that the somatic embryos obtained from resistant cell cultures were also resistant to the fungal filtrate. Furthermore, these resistant somatic embryos were observed to withstand a concentration of *E. ampelina* culture filtrate that was equal to that withstood by their progenitor resistant embryogenic cells and embryogenic cell masses.

Pathogen-Resistant Plants

Embryogenic cultures were selected in vitro against fungal culture filtrate produced by *E. ampelina*. Plants were regenerated from the selected cultures and acclimatized in the greenhouse. Plants from selected lines and unselected controls were sprayed with a spore suspension ($1 \times 10^6$ spores/mL) until runoff. The plants were individually bagged to maintain humidity (a condition is optimum for the pathogen to cause anthracnose disease) for 3 days. The bags were then removed and the plants were scored for anthracnose symptoms. All of the unselected controls exhibited a very high degree of susceptibility, and in most cases there was defoliation due to the disease within three days. Among the 40 different plants from the two selected lines, only one plant showed mild anthracnose symptoms. These data show that the resistance acquired by the embryogenic cells during in vitro selection can be translated into whole plant resistance against the pathogen.

In Vitro Selection and Establishment of Resistant Lines

Figure 2:
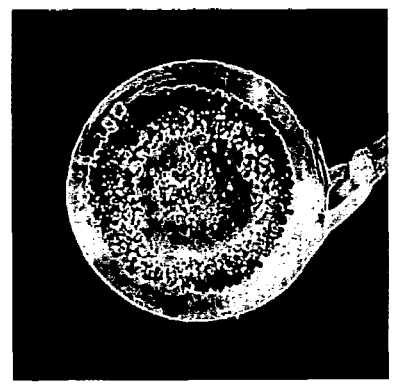
FIG. 2 shows growth of resistant proembryogenic masses in suspension culture after 4 cycles (10 days each) of in vitro selection with medium containing 40% *Elsinoe ampelina* culture filtrate.

PEMs became brown and necrotic within a few days of culture in culture filtrate-containing medium. The medium also turned dark brown in these flasks. As selection progressed, browning of the medium was gradually reduced, which was accompanied by necrosis of most of the PEMs. Only a few PEMs (or cells within a few PEMs) survived selection pressure through four or five cycles of selection (FIG. 2). Cultures that survived four and five cycles of selection were designated as 'resistant culture 1' (RC1) and 'resistant culture 2' (RC2), respectively. By continuous subculturing of these resistant cultures in suspension, we increased the tissue mass in approximately 5 months after withdrawing selection pressure. These cultures were used in subsequent studies and for plant regeneration. There was no browning in cultures that were grown in medium containing 40% (v/v) of Czapek-Dox broth. PEMs in these flasks grew normally as in the non-selected controls. This indicates that the necrosis was caused by compounds, that were produced by the fungus and released into the culture filtrate.

Dual Culture

Figure 3A:
FIGS. 3A and 3B are photographs showing inhibition of mycelial growth in dual culture by in vitro selected line. In vitro selected (left) and non-selected (right) PEMs from suspension were cultured in semisolid medium for 6 weeks and a small mycelial plug (5 mm diameter) was placed at the center after 6 weeks. Photograph taken 10 days after fungal inoculation.
Figure 3B:

Mycelium of *E. ampelina* grew uninhibited on plates containing PEMs and somatic embryos from non-selected control. Within a week after fungal inoculation, mycelium covered the entire plate, growing on the embryogenic tissue as well. However, both selected lines (RC1 and RC2) inhibited the growth of mycelium significantly (FIG. 3A). Even after 10 days, the mycelial growth did not reach the PEMs. A clear zone of inhibition could be observed for several days. A similar trend was observed with *F. oxysporium*, which is not a pathogen of grapevine (FIG. 3B). Mycelial growth was white, fluffy and rapid on the non-selected controls. On the selected lines, however, the fluffy growth was restricted to the central region of the plate. There was more vertical mycelial growth compared to the concentric pattern seen with non-selected control.

Conditioned Medium Test

Figure 4:
FIG. 4 is a photograph showing mycelial growth inhibition of *E. ampelina* in conditioned medium assay. Spent liquid medium, after growing in vitro selected (RC1 and RC2) and non-selected (C) PEMs in suspension, was solidified on glass cover slips, with potato dextrose agar to give a final strength of 0.75N. Mycelial plug of *Elsinoe ampelina* was inoculated and allowed to grow on the plates. Photographed two weeks after fungal inoculation.

The fungus grew well on coverslips bearing PDA or conditioned medium from non-selected controls. There was no difference in growth between the two. On the other hand, mycelial growth was inhibited on coverslips with conditioned medium from both resistant lines (FIG. 4). Microscopical examination revealed that the hyphal tips were smaller and many had burst, probably soon after they started growing onto these coverslips. Additionally, mycelial growth was uninhibited around these coverslips. This suggests that the coated coverslips contained anti-fungal compounds that had been secreted into the culture medium by selected cultures.

Electrophoresis of Extracellular Proteins

Figure 5A:
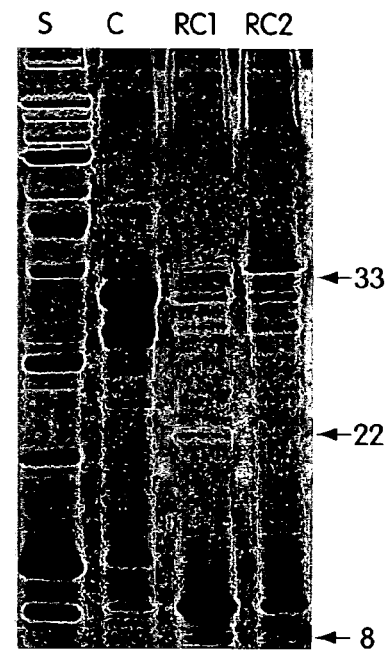
FIGS. 5A–5C are photographs of SDS-PAGE of extracellular proteins precipitated from spent liquid medium after growing selected and non-selected PEMs (FIG. 5A), somatic embryos (FIG. 5B), and inter-cellular washing fluids (ICWF) (FIG. 5C) in suspension culture. The gels were silver stained. Lanes (S) molecular weight markers, (C) non-selected control, (1) resistant line RC1, (2) resistant line RC2.
Figure 5B:
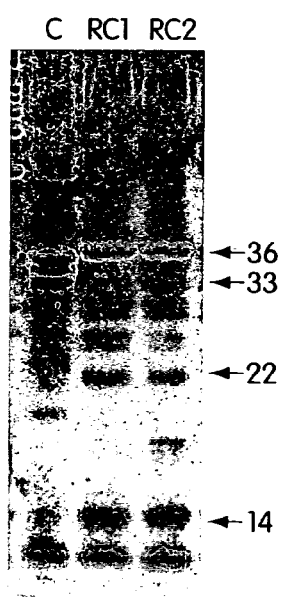

Significant differences in extracellular protein profile between the in vitro selected lines and non-selected controls could be seen in the SDS-PAGE, both in PEMs and differentiated somatic embryos. PEMs of both selected lines secreted additional proteins of 8, 22 and 33 kDa (FIG. 5A). Heart stage somatic embryos of non-selected controls exhibited two proteins of 35 and 36 kDa, while there was only one protein of 36 kDa in the selected lines (FIG. 5B). In addition, the 22 and 33 kDa proteins secreted by PEMs of selected lines were also present during this stage of embryogenesis, but the 8 kDa protein was absent. It is possible that this protein was present, but ran out of the gel, since shorter electrophoretic runs could not resolve this region adequately.

Chitinase Activity in Extracellular Proteins

Native PAGE, which can resolve even isozymes of the same size, indicates that selected lines have multiple chitinases. Two of these are induced by selection. One isozyme, with the least mobility, was greatly elevated in the selected lines in comparison with the control. After SDS-PAGE analysis, a 36 kDa protein exhibited chitinase activity in both selected lines and the non-selected controls as revealed by glycol chitin gel assay. At least a twenty-fold increase in chitinase activity of the 36 kDa isozyme was seen in the resistant lines as revealed by densitometric analysis. A 28 kDa protein also showed chitinase activity in the resistant lines. The results indicate that new isozymes of chitinases are expressed after selection and that the secretion of chitinase increases after in vitro selection in grapevine embryogenic cultures.

Immunological Detection of Chitinase

The 36 kDa protein in the ECP of both resistant lines strongly reacted with chitinase antiserum. There was no reaction in the ECP of non-selected controls, though chitinase activity was detected in the glycol chitin assay. This indicates that the 36 kDa protein observed in the non-selected control and in the selected lines may not be the same protein. The 28 kDa peptide that was present in the selected lines as detected in the glycol chitin assay, did not react with this antiserum.

Retesting of Somatic Embryos after In Vitro Selection

Figure 7:
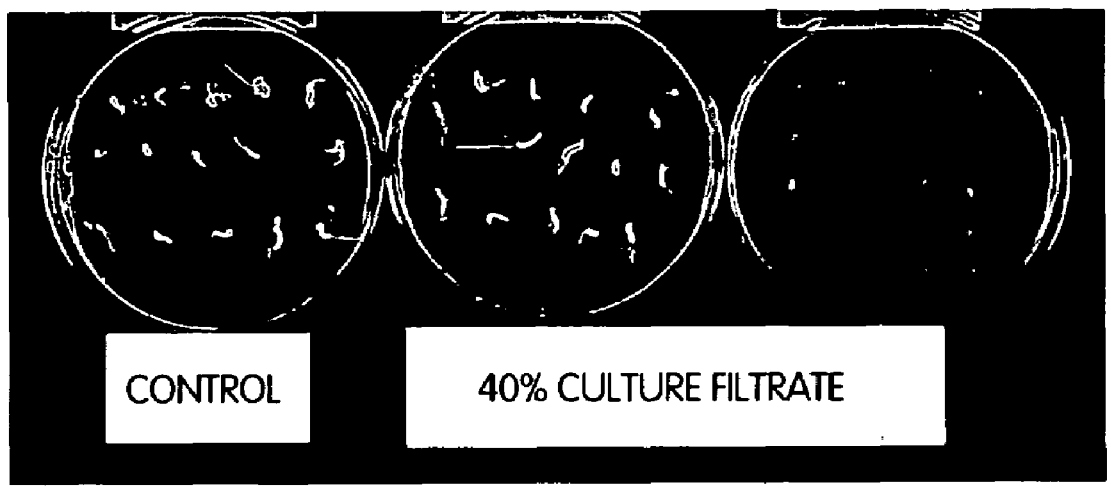
FIG. 7 shows mature somatic embryos of selected and non-selected cultures growing in solid medium containing 40% (v/v) *Elsinoe ampelina* culture filtrate. (Left) Somatic embryos of R1 in regular embryogenesis medium, (Center) Somatic embryos of RC1 in embryogenesis medium containing 40% (v/v) culture filtrate, (Right) Somatic embryos of non-selected control in embryogenesis medium containing 40% (v/v) culture filtrate.

Mature somatic embryos of non-selected controls grew normally on germination medium, but they did not germinate on medium containing 40% (v/v) fungal culture filtrate. Most of them turned necrotic within 4 days after culture. Somatic embryos from both resistant lines germinated and grew into plants on both media (FIG. 7), indicating that the acquired resistance is stable and not epigenetic. More than 50 plants were regenerated from somatic embryos from each of the resistant lines and established in the greenhouse. Plant establishment was accomplished at 8 months after selection and testing of plants occurred when they were 18 months old.

In Vitro Leaf Bioassay

Leaves from non-selected controls developed black lesions at the infected sites within three days of spore inoculation. The lesions spread rapidly and the entire leaf became necrotic within a week. Leaves from both in vitro selected lines were very slow in exhibiting the lesions. It took more than 10 days for the lesions to appear. The lesions did not spread as in the controls, even after two weeks of incubation, indicating that the resistance acquired by PEMs during in vitro selection persisted in the plants.

Testing the Regenerated Plants for Resistance

Figure 8:
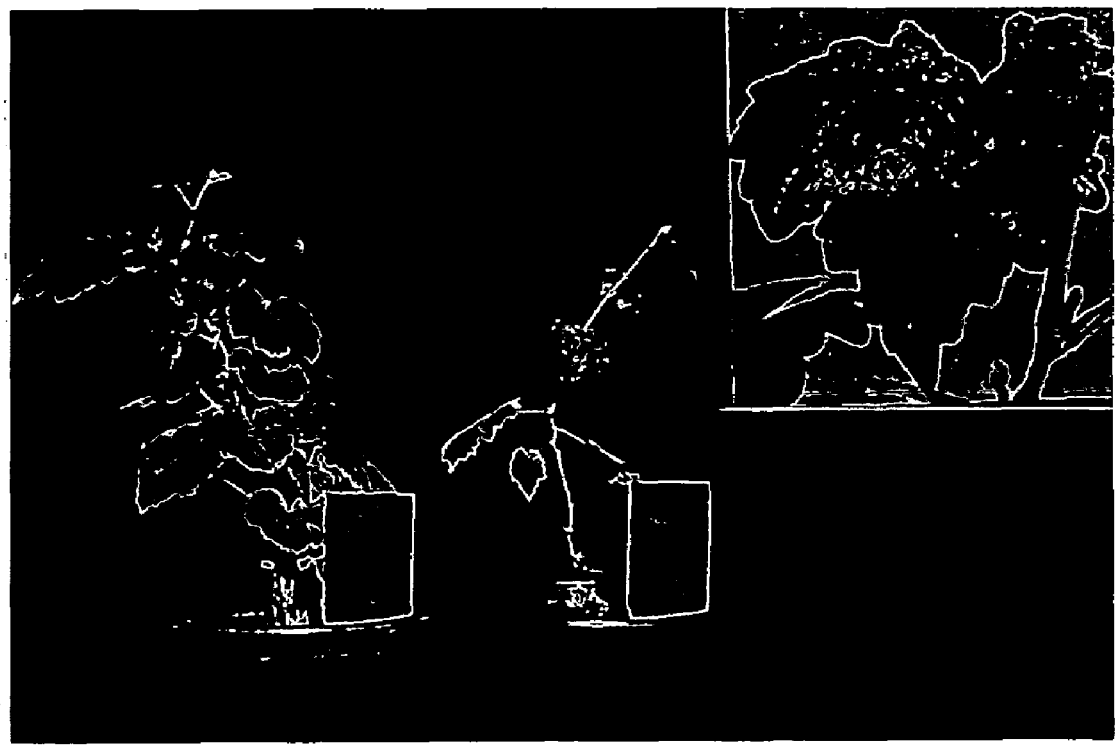
FIG. 8 shows greenhouse grown, somatic embryo derived plants of selected and non-selected cultures were sprayed with *Elsinoe ampelina* spore suspension ($1 \times 10^6$ spores per ml). Plants from non-selected somatic embryos exhibited anthracnose symptoms 4 days after inoculation (inset), while the in vitro selected plant did not show any symptom.

After removing bags, the leaves of inoculated plants were examined for disease symptoms. Most of the young leaves from non-selected control plants were crinkled with spreading lesions. Some leaves exhibited 'shothole symptoms', characteristic of anthracnose disease (FIG. 8). Few leaves turned necrotic within this three day period. There was extensive defoliation among non-selected controls. Thirty nine out of forty in vitro selected plants from both resistant lines remained healthy even after several days. Only one plant tested this way showed mild symptoms of leaf curl; no lesions were observed, however. Defoliation was very minimal and often only the older leaves were lost.

Re-Isolation of Fungus from the Infected Plants

Fungal mycelium grew rapidly from symptomatic leaves of control plants. Mycelial growth was identical to that of the original control culture. Microscopic observations of conidia confirmed them to be E. ampelina. Koch's postulate was accomplished using these conidia to infect grapevine leaves.

Identification of Differentially Expressed Proteins

Extracellular proteins from resistant and control embryogenic cultures were analyzed to determine if any activation of defense genes was apparent in the embryogenic cells or somatic embryos resistant to E. ampelina. Analysis of extracellular proteins (i.e., proteins secreted in the liquid culture medium) revealed changes in protein profiles between the control and resistant embryogenic cultures. In addition, chitinase was observed to be secreted in abundance by the resistant embryogenic cultures in comparison with control cultures. This secretion of chitinase was observed even eight months after selection. These results demonstrated that the resistant cultures retained an activity many generations (in terms of cell divisions) after the selection pressure had been removed; hence, the E. ampelina resistance was a stable genetic mutation.

Figure 5C:
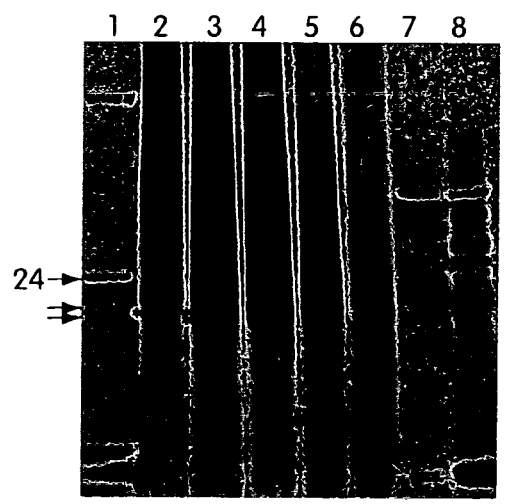
Figure 6A:
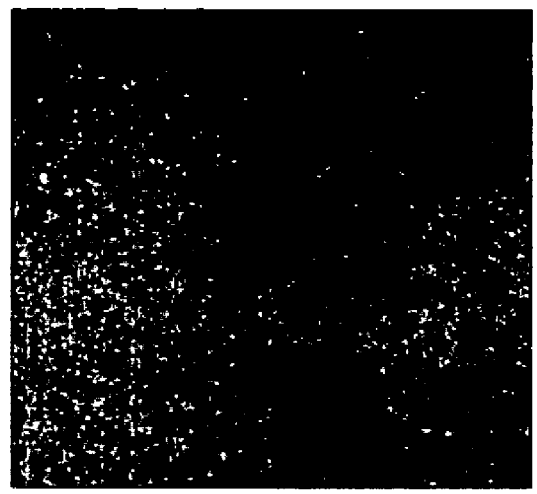
FIGS. 6A and 6B show chitinase activity in the extracellular proteins precipitated from spent liquid medium after growing selected and non-selected PEMs in suspension culture. Chitinase activity was detected after native PAGE (FIG. 6A) or SDS-PAGE (FIG. 6B) using a glycol chitin assay. Lanes (c) non-selected control, (s) Chitinase standard from *Serratia marcescens* (Sigma, St. Louis, Mo.) (1) resistant line RC1 (2) resistant line RC2.
Figure 6B:
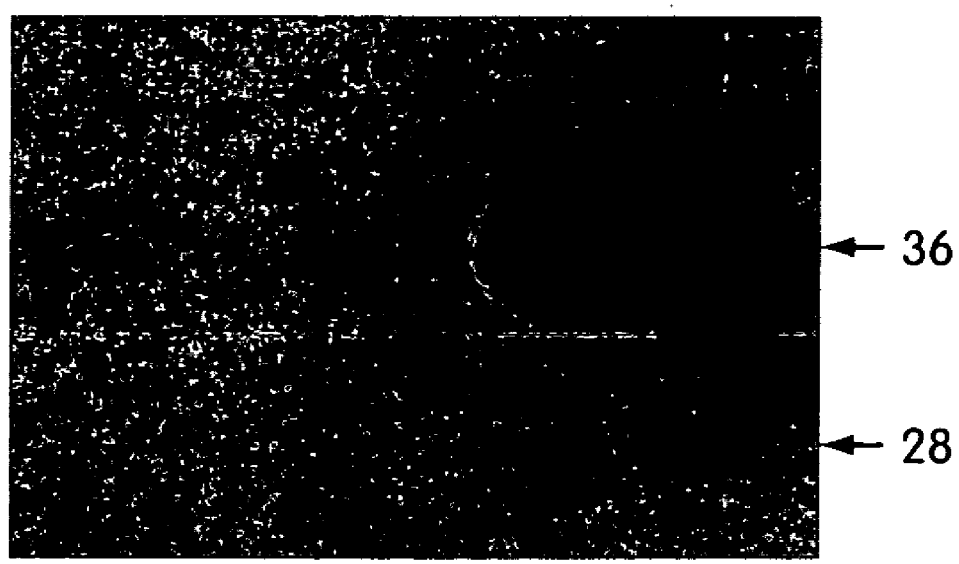

Extraction of proteins in the intercellular fluids was more difficult than described for other species. Extracted proteins are preferably separated by electrophoresis within a few hours, since storing them even at −50° C. leads to loss of proteins. ICWF extractions were analysed several times in order to confirm the separation of proteins. Two prominent, differentially expressed, proteins of 8 and 22 kDa could be identified consistently in the ICWF of selected lines. While there were two proteins of 1.6 and 22 kDa in the ICWF of RC1 and RC2, a weak 21.6 kDa protein was present in the ICWF of non-selected control plants (FIG. 5C).

Immunodetection

Figure 10A:
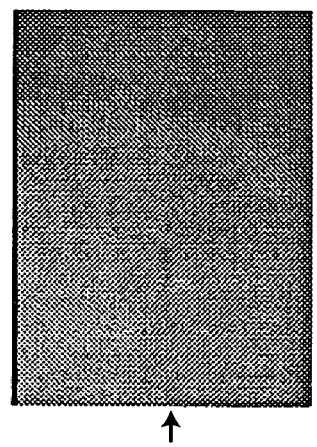
FIGS. 10A–10C are a series of photographs showing immuno-detection of a 22 kDa protein with PR-5 antiserum. Extracellular proteins (ECPs) from PEMs and heart stage somatic embryos were separated by SDS-PAGE on a 12% mini-gel and transferred to a ImmunBlot™ membrane and detected with PR-5 antiserum from 'Pinto bean'. Proteins from PEMs are shown in FIG. 10A, heart stage somatic embryos in FIG. 10B, and ICWF of regenerated plants in FIG. 10C. Lanes: C—non-selected control, RC1—in vitro selected line 1, and RC2—in vitro selected line 2.
Figure 10B:
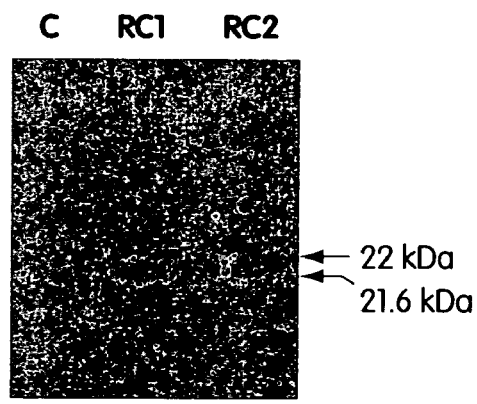
Figure 10C:
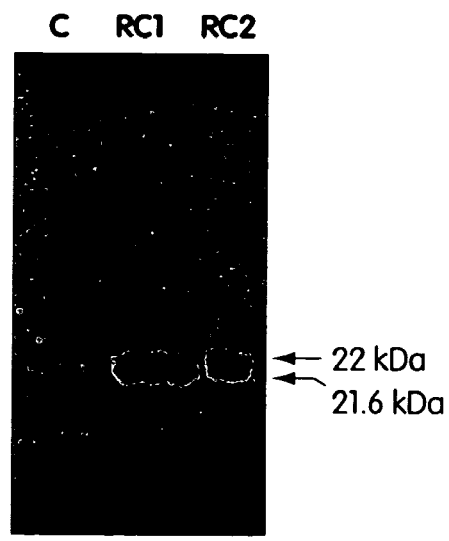

The 22 kDa protein from both resistant lines reacted with pinto bean PR 5 antiserum. There was no reaction in the control. This protein could be detected both at the PEM stage (FIG. 10A) and also at the heart stage somatic embryo, using the same antiserum, indicating persistent expression of this protein. At the somatic embryo stage, however, an additional band of approximately 26 kD also cross reacted with this antiserum (FIG. 10B) in the resistant line RC2. There were two bands of 22 and 23 kDa (referred to herein as the 22 kDa doublet) in the ICWF from plants of both resistant lines that reacted with the PR-5 antiserum. There was also faint reaction in the ICWF from non-selected controls (FIG. 10C). Thus there is a doublet between 22 kDa and 23 kDa that includes two PR-5-related proteins.

Identification of Differentially Expressed Proteins Using N-terminal Amino Acid Sequencing The sequence of the N-terminal 21 amino acids of the 8 kDa protein was determined by Edman degradation method to be TVTXGQVASAVGPXISYLQ (SEQ ID NO: 1). Sequence similarity searches revealed that this protein exhibits a high similarity with non-specific lipid transfer proteins (nsLTP). Among the nsLTPs that showed high similarity was a 9 kDa protein identified from grapevine somatic embryos and identified as LTP P4 (Coutos-Thevenot et al., Eur. J. Biochem. 217:885–889, 1993). In additon, it also exhibited 75% similarity with another 9 kDa protein from grapevine berries (Salzman et al., supra). Thus the 8 kDa protein was identified as a nsLTP (FIG. 11). Amino acid sequence information could not be obtained for the 14 kDa protein that was differentially expressed by heart stage somatic embryos presumably because the N-terminus of this protein was blocked.

One of the N-terminal amino acid sequences (AT-FDILNKXTYTVXA; SEQ ID NO: 2) of the 22 kDa protein doublet secreted by heart stage somatic embryos of in vitro selected lines matched that of a thaumatin/osmotin-like protein (VVTL-1) isolated from grapevine berries (Tattersal et al., Plant Physiol. 114:759–769, 1997). In addition, it also exhibited very high sequence similarity with the N-terminal sequences of several other TLPs. Among these, two tobacco thaumatin-like proteins, E22 and E2, exhibited 92% sequence similarity (FIG. 12). The amino fragment from the second protein (ATFNIQNKGGYTVXA; SEQ ID NO: 3) had homology to grapevine osmotin. Both proteins from ICWF exhibited high homology with the corresponding 22 kDa protein doublet secreted by heart stage somatic embryos. It is evident that the 22 kDa protein doublet is differentially and constitutively expressed by the selected lines, predominantly as a secreted protein and could be traced from the early PEM stage to all the way in regenerated plants.

N-terminal sequence of the 33 kDa protein from heart stage embryos (ASLADQQANEFTKV; SEQ ID NO: 4) did not reveal any significant sequence similarity in the database search. A cDNA encoding the 33 kDa protein was cloned as follows. Primers were designed based on amino terminal and carboxy terminal amino acid sequence information generated from the 33 kDa protein. Using these, we amplified the fragment from the genomic DNA and then cloned and sequenced the fragment. The primer designed based on the carboxy terminal fragment did not help in amplifying, but a palindromic sequence to the primer designed based on the N terminal fragment existed at the 3' end of the DNA sequence. The sequences for both the DNA (SEQ ID NO: 6) and the putative protein (SEQ ID NO: 5) are depicted in FIG. 9.

Pathogen Resistance

The methods of the invention are useful for providing resistance to other grapevine diseases. Grape plants exhibiting resistance to a number of different diseases may be generated from embryogenic cells and embryogenic cell masses that are selected for resistance to the etiologic agent of a particular disease, a toxin produced by the agent, or the etiologic agent (or toxin) of another grapevine disease. For example, embryogenic cells and embryogenic cell masses may be grown in a liquid suspension culture in the presence of a filter-sterilized culture filtrate prepared from a pathogen, at a concentration of culture filtrate that is ideal for in vitro selection. After four or five cycles of recurrent selection in such a liquid medium containing culture filtrate, with sub-culturing performed every ten days as described above, the surviving cells are allowed to expand in a liquid medium lacking the culture filtrate. From these cells, somatic embryogenesis may be performed to produce cells and plants showing increased resistance to the powdery mildew disease, as well as to diseases caused by other fungi and/or bacteria. The filtrate may be the cell supernatant from the culture. In some cases, it may be preferable to culture the pathogen in the presence of plant cells, harvest and lyse and/or homogenize the cells, and then collect the supernatant following centrifugation. Such a filtrate is particularly useful when the pathogen is a virus or a bacterium.

The method described herein can be modified to select for cells that have been transformed with a nucleic acid sequence. Cell transformation, while a standard technique, does not result in every cell containing the nucleic acid of interest. It is standard laboratory practice to include in the transformation nucleic acid sequence that confers a growth advantage in a specific selection medium. Thus, only the cells of interest (i.e., the ones that are transformed) are able to grow or survive in the selection medium. The proteins described herein (and the nucleic acids encoding them) can be used as selectable markers in such methods. In this example, the selection medium includes a pathogen, or a pathogen filtrate or conditioned medium. Cells that have been transformed with the nucleic acid sequence encoding the protein that confers pathogen resistance will survive, while cells that have not been transformed will die.

It will be understood that a protein that confers resistance to one pathogen may also confer resistance to additional pathogens. Plants resistant to anthracnose may be additionally resistant to additional pathogens. For example, a plant that is resistant to both anthracnose and black rot (caused by the fungus, *Guignardia bidwellii*) may be additionally resistant to *Botrytis* bunch rot and blight (caused by the fungus, *Botrytis cinerea*). The rapid generation of these resistant grape plants using the methods of the invention allows for such combination of resistance not just for fungi, but for other grapevine pathogens (e.g., bacteria and viruses).

Evaluation of the level of pathogen protection conferred to a plant by the selection methods described herein is determined according to conventional methods.

EXAMPLE 5

Grapevine Transformation

The method described herein can be used to produce transformed plants. Cells can be transformed at any step in the process of making a somatic embryo-derived. Thus, tissue or cells suitable for transformation include explanted tissue, embryogenic cells, embryogenic cell masses, and somatic embryos (including mature somatic embryos).

Cell cultures produced according to the methods of the invention may be transformed with DNA comprising a desired transgene, such as the DNA of SEQ ID NO: 6). Such cells, for example, may be transformed with genes which confer resistance to pathogens, diseases, or pests, or any combination thereof. For example, a number of *Bacillus thurigiensis* genes which encode proteins that are toxic to a number of pests are well known and useful in the methods of the invention. Several standard methods are available for introduction of a transgene into a plant host, thereby generating a transgenic plant.

Upon construction of the plant expression vector, several standard methods are available for introduction of the vector into a plant host, thereby generating a transgenic plant. These methods include (1) *Agrobacterium*-mediated transformation (*A. tumefaciens* or *A. rhizogenes*) (see, e.g., Lichtenstein and Fuller In: *Genetic Engineering*, vol 6, P W J Rigby, ed, London, Academic Press, 1987; and Lichtenstein, C. P., and Draper, J, In: *DNA Cloning*, Vol II, D. M. Glover, ed, Oxford, IRI Press, 1985)); (2) the particle delivery system (see, e.g., Gordon-Kamm et al., *Plant Cell* 2:603 (1990); or BioRad Technical Bulletin 1687, supra); (3) microinjection protocols (see, e.g., Green et al., supra); (4) polyethylene glycol (PEG) procedures (see, e.g., Draper et al., *Plant Cell Physiol.* 23:451, 1982; or e.g., Zhang and Wu, *Theor. Appl. Genet.* 76:835, 1988); (5) liposome-mediated DNA uptake (see, e.g., Freeman et al., *Plant Cell Physiol.* 25:1353, 1984); (6) electroporation protocols (see, e.g., Gelvin et al., supra; Dekeyser et al., supra; Fromm et al., *Nature* 319:791, 1986; Sheen *Plant Cell* 2:1027, 1990; or Jang and Sheen *Plant Cell* 6:1665, 1994); and (7) the vortexing method (see, e.g., Kindle supra). The method of transformation is not critical to the invention. Any method which provides for efficient transformation may be employed. As newer methods are available to transform crops or other host cells, they may be directly applied.

The following is an example outlining one particular technique, an *Agrobacterium*-mediated plant transformation. By this technique, the general process for manipulating genes to be transferred into the genome of plant cells is carried out in two phases. First, cloning and DNA modification steps are carried out in *E. coli*, and the plasmid containing the gene construct of interest is transferred by conjugation or electroporation into *Agrobacterium*. Second, the resulting *Agrobacterium* strain is used to transform plant cells. Thus, for the generalized plant expression vector, the plasmid contains an origin of replication that allows it to replicate in *Agrobacterium* and a high copy number origin of replication functional in *E. coli*. This permits facile production and testing of transgenes in *E. coli* prior to transfer to *Agrobacterium* for subsequent introduction into plants. Resistance genes can be carried on the vector, one for selection in bacteria, for example, streptomycin, and another that will function in plants, for example, a gene encoding kanamycin resistance or herbicide resistance. Also present on the vector are restriction endonuclease sites for the addition of one or more transgenes and directional T-DNA border sequences which, when recognized by the transfer functions of *Agrobacterium*, delimit the DNA region that will be transferred to the plant.

In another example, plant cells may be transformed by shooting into the cell tungsten microprojectiles on which cloned DNA is precipitated. In the Biolistic Apparatus (Bio-Rad) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to pass through. As a result, the plastic macroprojectile smashes against the stopping plate, and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

In general, transfer and expression of transgenes in plant cells are now routine practices to those skilled in the art, and have become major tools to carry out gene expression studies in plants and to produce improved plant varieties of agricultural or commercial interest.

While the expression of one of the proteins of the invention is likely to confer on a plant increased disease resistance, it may be preferable to express two, three, or even all four proteins in a plant to achieve maximal pathogen resistance. This can be achieved either by the selection method described herein, or by producing a plant having transgenes encoding the four sequences.

EXAMPLE 6

Generation of Antibodies, Nucleic Acids, and Proteins

Using standard techniques, such as those described above, one in the art can identify full-length proteins and nucleic acids from any variety of grape plant. For example, an amino terminal peptide fragment can be used to generate a degenerate nucleic acid probe for PCR, Southern blotting, or colony hybridization. Using a nucleic acid sequence, one can identify orthologues in other variety of plants or in plants other than grape plants. The proteins or polypeptides of the invention can be used to raise antibodies or binding portions thereof or probes. The antibodies can be monoclonal or polyclonal. A description of the theoretical basis and practical methodology of fusing such cells is set forth in Kohler and Milstein, Nature, 256:495, 1975), and Milstein and Kohler, Eur. J. Immunol., 6:511, 1976), hereby incorporated by reference. Procedures for raising polyclonal antibodies are also well known to the skilled artisan. This and other procedures for raising polyclonal antibodies are disclosed in Harlow et. al., editors, Antibodies: A Laboratory Manual (1988), which is hereby incorporated by reference.

In addition to utilizing whole antibodies, binding portions of such antibodies can be used. Such binding portions include Fab fragments, F(ab')$_2$ fragments, and Fv fragments. These antibody fragments can be made by conventional procedures, such as proteolytic fragmentation procedures, as described in Goding, *Monoclonal Antibodies: Principles and Practice*, New York: Academic Press, pp. 98–118 (1983), hereby incorporated by reference.

The present invention also relates to probes found either in nature or prepared synthetically by recombinant DNA procedures or other biological procedures. Suitable probes are molecules which bind to the proteins of the present invention. Such probes can be, for example, proteins, peptides, lectins, or nucleic acid probes.

Antibodies raised against the proteins or polypeptides of the present invention or binding portions of these antibodies can be utilized in a method for selection of plants having increased resistance to a plant pathogen. A variety of assay systems can be employed, such as enzyme-linked immunosorbent assays, radioimmunoassays, gel diffusion precipitin reaction assays, immunodiffusion assays, agglutination assays, fluorescent immunoassays, protein A immunoassays, or immunoelectrophoresis assays.

The sequences of the present invention can also be used to identify proteins that are substantially identical to those described herein. By "substantially identical" is meant a protein or nucleic acid exhibits at least 70%, preferably 80%, and most preferably 90%, 95%, or even 98% identity to a reference amino acid sequence or nucleic acid sequence. For proteins, the length of comparison sequences will generally be at least 15 amino acids, preferably at least 20 amino acids, more preferably at least 25 amino acids, and most preferably 35 amino acids or greater. For nucleic acids, the length of comparison sequences will generally be at least 50 nucleotides, preferably at least 60 nucleotides, more preferably at least 75 nucleotides, and most preferably 110 nucleotides or greater.

Sequence identity, at the amino acid levels, is typically measured using sequence analysis software (for example, Sequence Analyis Software Package of the Genetics Computer Group, Univerity of Wisconsin Biotechnology Center, 1710 University Avenue, Madison, Wis. 53705, BLAST, or PILEUP/PRETTYBOX prgrams). Such software matches identical or similar sequences by assigning degrees of homology to various substitutions, deletions, and/or other modifications.

The present invention also includes nucleic acids that selectively hybridize to the DNA sequence of the present invention. Hybridization may involve Southern analysis (Southern Blotting), a method by which the presence of DNA sequences in a target nucleic acid mixture are identified by hybridization to a labeled oligonucleotide or DNA fragment probe. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe as described in Sambrook et al., (1989) *Molecular Cloning*, 2nd edition, Cold Spring Harbor Laboratory, Cold Spring Harbor, N.Y.

Hybridization often includes the use of a probe. It is generally preferred that a probe of at least 20 nucleotides in length be used, preferably at least 50 nucleotides, more preferably at least about 100 nucleotides.

A nucleic acid can hybridize under moderate stringency conditions or high stringency conditions to a nucleic acid disclosed herein. High stringency conditions are used to identify nucleic acids that have a high degree of homology or sequence identity to the probe. High stringency conditions can include the use of a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, and 75 mM sodium citrate at 42° C. Another example is the use of 50% formamide, 5×SSC (0.75 M NaCl, 0.075 M sodium citrate), 50 mM sodium phosphate (pH 6.8), 0.1% sodium pyrophosphate, 5× Denhart's solution, sonicated salmon sperm DNA (50 ug/mL) 0.1% SDS, and 10% dextran sulfate at 42° C., with washes at 42° C. in 0.2×SSC and 0.1% SDS. Alternatively, low ionic strength washes and high temperature can be employed for washing.

Moderate stringency conditions are hybridization conditions used to identify nucleic acids that have less homology or identity to the probe than do nucleic acids under high stringency. All of these techniques are well known to the artisan skilled in molecular biology.

Materials and Methods

In Vitro Selection, Culture Establishment and Plant Regeneration

Suspension cultures, somatic embryogenesis and plant regeneration of 'Chardonnay' (Clone 02Ch; Stimson Lane Wineries, Prosser, Wash.) consisting of actively growing PEMs were established as follows. Log phase cultures were sieved using a 960 μM sieve to generate a synchronized culture. Approximately 1.0 g of PEMs were subjected to recurrent selection in suspension culture with a modified culture medium containing 40% (v/v) fungal culture filtrate. The liquid medium was prepared and cooled to room temperature and the culture filtrate was added after filter sterilization to eliminate any loss of filtrate activity due to autoclaving. The culture filtrate was obtained by growing a virulent strain of E. ampelina spores for 3 weeks in Czapek-Dox broth. Cell free extract was collected and stored at −20° C. until further use. The pH of the culture was adjusted to 5.8 before adding to the medium. Selection was carried out for four or five cycles, each cycle lasting for 10 days. At the end of $4^{th}$ and $5^{th}$ cycles, putative resistant cultures were proliferated in regular suspension culture medium and established as 'resistant culture 1' (RC1) and 'resistant culture 2' (RC2), respectively. Somatic embryogenesis was achieved by culturing the selected PEMs in auxin-free suspension culture medium and the resulting somatic embryos were germinated in solid medium. Regenerated plants were acclimatized in potting mixture and established in a greenhouse. A set of control, non-selected PEMs were cultured in a similar way and plants regenerated from these non-selected cultures served as control for rest of the experiments.

Dual Cultures

PEMs of resistant and unchallenged controls, both of which were maintained in suspension culture for more than 20 weeks after selection, were used for dual culture. PEMs were collected on a sterile filter paper and approximately 1.0 g of PEMs were cultured on semisolid medium at opposite sides of a 100×15 mm petri dish. The medium had the same components as liquid medium, but was solidified with TC agar at 7.0 g/l. The cultures were sealed with Parafilm™ and incubated in darkness at 25±2° C. After 5 weeks, a mycelial plug (5 mm in diameter) from an actively growing fungal culture was placed at the center of the plates. Cultures were tested against two different fungi, E. ampelina (against which the PEMs were selected) and Fusarium oxysporium (a root pathogen isolated from watermelon). After inoculating mycelial plugs the cultures were sealed and incubated at 25±2° C. at 16 h photoperiod. There were 5 petri plates for each fungus and the experiment was repeated twice. Mycelial growth on the plates was measured daily and photographed after 10 days of culture.

Conditioned Medium Assay

Spent liquid medium was collected from a resistant line and unchallenged control and centrifuged at 2500 rpm for 10 min to remove cellular debris. After filter-sterilization, the supernatant was diluted with an equal volume of warm, 1.5 N (58.5 gl$^{-1}$) potato dextrose agar (PDA) medium to give a final concentration of 0.75 N (29.25 gl$^{-1}$). Sterile glass slide coverslips were soaked in the molten medium rapidly (before the medium solidified) and placed on 0.75 N PDA plates. Three coverslips were placed on each plate. Coverslips soaked in 0.75 N PDA and plated as before served as an additional control. After cooling the plates overnight, a mycelial plug from E. ampelina was placed at the center of the plate and incubated at 25±2° C. Mycelial growth on the coverslips containing the conditioned medium was evaluated daily and photographed after seven days of culture.

Extraction of ECPs

Spent medium was collected in sterile flasks during subculture and filtered through a double layer Kimwipe™ to eliminate any cellular debris. ECP was precipitated from the filtered medium by adding three volumes of ice cold, 95% ethanol and kept overnight at 0° C. Proteins were pelleted by centrifugation, concentrated in a vacuum concentrator and resuspended in sterile distilled water. Protein quantitation was done by the Bradford protein assay, using bovine serum albumin as a standard. Protein samples were stored at −20° C. until further use.

Extraction of ICWF and Protein Concentration

Fully expanded, flaccid leaves were collected from greenhouse-grown plants early in the morning. The leaves were washed thoroughly with distilled water and blot-dried. Lamina were cut into 2 cm wide strips and vacuum infiltrated for 15 min in a buffer containing 100 mM Tris-HCl, 2.0 mM CaCl$_2$, 10 mM EDTA, 50 mM P-mercaptoethanol and 0.5 M sucrose, at the rate of 10 ml/g of leaf tissue. After infiltration, the leaf strips were gently blotted and rolled into 0.5 ml microfuge tubes (without caps) with a 0.2 mm dia hole at the bottom. Only 2–3 strips were loaded in each microfuge tube. These tubes were then loaded onto a 1.5 ml centrifuge tubes. The set-up was spun at 7500 rpm for 15 min at room temperature. ICWF collects as a dense drop in the 1.5 ml centrifuge tubes. To concentrate the proteins, ICWF was diluted with 4 volumes of distilled water and the proteins were precipitated with 3 volumes of ice-cold, 95% ethanol overnight at 0° C. Proteins were pelleted by centrifugation, concentrated in a vacuum concentrater and resuspended in sterile distilled water.

Electrophoresis of Proteins

SDS-PAGE was carried out using 1 mm thick mini gels. Protein samples were diluted with equal volume of SDS-PAGE buffer (Sigma, St. Louis, Mo.) and the diluted samples were heated in a boiling water bath for 5 min and cooled. Samples were spun at 10,000 rpm for 5 min at room temperature to remove any insoluble particles. Total protein of 10 μg was loaded onto each lane and electrophoresed for approximately 80 min at 200 V. The gels were then either silver-stained using SilverSnap™ (Pierce, Rockford. Ill.) or stained with colloidal Coomassie Blue (Sigma, St. Louis Mo.) and photographed using a Kodak DC 120 digital camera.

Chitinase activity was analyzed as follows. After native PAGE, the gels were rinsed in 150 μM sodium acetate (pH 5.0) for 15 min. The gels were placed on a clean glass plate and overlaid with a 7.5% gel containing 0.01% (v/v) glycol chitin. After removing air bubbles, the gel sandwich was incubated at 37° C. under moist conditions. The overlay gels were removed and stained with 0.01% fluorescent brightener (Calcoflour white M2R) in Tris-HCl buffer (pH 8.9) for 10 min and rinsed thoroughly in distilled water overnight. Chitinase activity derived from various chitinase isozymes was visible as dark (lytic) bands in the overlay gels.

Running gels in SDS-PAGE were incorporated with 0.02% glycol chitin while casting the gels. After electrophoresis, the gels were incubated in 200 mM sodium acetate solution at pH 5.0 containing 1% of Triton-X 100 for 4 h at 37° C. After incubation, the gels were washed 3 times with distilled water, stained with 0.01% (v/v) fluorescent brightener in 500 mM Tris-HCl (pH 8.9) for 10 min and destained overnight in distilled water. Chitinase isozymes were identified as lytic bands on a UV-transilluminator and photographed using a Kodak DC 120 digital camera with orange filter.

Immunodetection of Chitinase

SDS-PAGE was carried out as described above and the proteins were transferred to a PVDF membrane (Bio-Rad, Almeda, Calif.) in a mini transblot gel transfer cell. Following transfer of proteins, the membrane was probed with an antiserum raised against a barley seed chitinase at 1:1000 dilution. The antigen-antibody complex was detected by a goat-anti rabbit horseradish peroxidase (Bio-Rad).

Re-Testing the In Vitro Selected Cultures for Resistance to Culture Filtrate

Mature somatic embryos from both selected cultures and non-selected control were germinated on a solid germination medium containing 40% (v/v) fungal culture filtrate. There were five plates per treatment, each containing 15 embryos. After culturing, the plates were incubated in the dark. Three weeks after incubation, embryos that germinated were counted as being resistant. A similar set of embryos were germinated in a medium without culture filtrate as an additional control.

Plant Regeneration and Establishment in Greenhouse

Plants regenerated from somatic embryos were transferred to starter plugs containing sterile commercial potting mixture and kept under 16 h photoperiod for in vivo acclimitization. After approximately one month, soil-acclimatized plants were transferred to the greenhouse. Well-established and vigorously growing plants, approximately 18 months after regeneration, were used for further studies.

In Vitro Leaf Bioassay for Anthracnose Resistance

Fully expanded green, young leaves, approximately 6 cm wide were collected from 10 different plants in each of two selected lines and the non-selected control. These leaves were inoculated with 100 µl of a spore suspension containing $1 \times 10^6$ spores per ml. There were three inoculations on each leaf in the inter-venal region. Immediately after inoculation, the leaves were incubated under humid conditions in moist chambers at 25+2° C. and 16 h photoperiod. After one week, the leaves were evaluated for anthracnose symptoms. The assay was repeated twice.

Test for Anthracnose Resistance in Selected Plants

Eighteen month old, greenhouse grown in vitro selected plants and non-selected controls regenerated from somatic embryos were used in this study. Clones from the original 'Chardonnay' ('02Ch'), from which the cultures were initiated, were also used as an additional control. Plants that were actively growing with young leaves were chosen for this test. The plants were sprayed with a spore suspension containing $1 \times 10^6$ spores per ml on both sides of the leaves until runoff. They were then individually covered with a polythene bag carefully so that leaves did not touch the bag which was sealed around the pot. These plants were incubated in the growth room, at 25+/−2° C. and 16 h photoperiod. After 72 h of incubation, the bags were carefully removed and the plants were observed for disease symptoms. Plants exhibiting crinkling of leaf lamina or typical shot hole symptoms were scored as susceptible. The experiment was repeated twice using different sets of plants from each selected line and control. For each test, there were at least 20 plants from each selected line and 6 plants from the control.

Recovery of Pathogen after Infection

Leaves that showed anthracnose symptoms were removed and washed well with distilled water. They were air dried under the laminar flow hood for two days. Pieces of lamina and midrib from these air dried leaves were then cultured in PDA. A small plug of mycelium from the original culture that was used to infect the leaves was also cultured, for comparison. The cultures were incubated at 16 h photoperiod and 25±2° C.

Immunodetection of Proteins

After SDS-PAGE, proteins were transferred to Immuno-Blot™ PVDF membrane (Bio-Rad, Almeda, Calif.) in a mini trans-blotter according to manufacturer's instructions. Transfer was carried out under high intensity electric field (100 V) for 2 hr. The membrane was washed thoroughly in washing buffer and rinsed thrice in distilled, deionized water for 10 min each, then blocked overnight in a 3% bovine serum albumin solution at room temperature. After another cycle of washing and rinsing, proteins were probed with PR 5 antiserum raised against pinto bean thaumatin-like protein (provided by Dr. O. P. Sehgal, University of Missouri, Columbia, Mo.) at a dilution of 1:500 for 2 hr at room temperature with gentle shaking. Color development was carried out using Opti-4Cn kit (Bio-rad, Almeda, Calif.), according to manufacturer's instructions.

N-Terminal Amino Acid Sequencing

For N-terminal amino acid sequencing, proteins were transferred to an ImmunoBlot PVDF membrane using a buffer lacking glycine. After transfer, proteins were stained with Coomassie blue and appropriate bands were identified based on their molecular weight and cut out using a sterile scalpel. Amino-terminal amino acid sequence determination was accomplished by the automated Edman degradation method, in the Protein Chemistry Core Laboratory, University of Florida, Gainesville, using a protein sequencer, Model 494HT (Applied Biosystems, Foster City, Calif.). Phenylthiohydantoin amino acid derivatives were automatically detected by a 120A analyzer used in conjunction with the sequencer.

Other Embodiments

All publications mentioned in this specification are herein incorporated by reference to the same extent as if each independent publication was specifically and individually indicated to be incorporated by reference.

While the invention has been described in connection with specific embodiments thereof, it will be understood that it is capable of further modifications. This application is intended to cover any variations, uses, or adaptations following, in general, the principles of the invention and including such departures from the present disclosure within known or customary practice within the art to which the invention pertains and may be applied to the essential features hereinbefore set forth.

What is claimed is:

1. A method of producing a grape somatic embryo having resistance to a phytotoxin, said method comprising the steps of
   (a) culturing a grape somatic embryo in a first liquid culture medium comprising a plant growth regulator and said phytotoxin;
   (b) exchanging said first liquid cluture medium for a second liquid culture medium not comprising said phytotoxin;
   (c) recovering a living grape cell or grape cell cluster from said second liquid culture, said living cell or cell cluster being resistant to said phytotoxin; and
   (d) culturing said grape cell or grape cell cluster in a third culture medium to produce a grape somatic embryo;
wherein said phytotoxin is from *Elsinoe ampelina*.

2. The method of claim 1, further comprising the step of (e) transferring said grape somatic embryo to a germination medium to grow a grape plant.

3. The method of claim 1, wherein said plant growth regulator of step (a) is an auxin.

4. The method of claim 1, wherein steps (a)–(d) are repeated in sequence at least four times.

5. The method of claim 1, wherein said culture step (a) is for at least five consecutive days.

* * * * *